United States Patent
Hosoe et al.

(10) Patent No.: US 10,525,138 B2
(45) Date of Patent: Jan. 7, 2020

(54) COMPOUND AS CATIONIC LIPID

(71) Applicant: Kyowa Hakko Kirin Co., Ltd., Tokyo (JP)

(72) Inventors: Shintaro Hosoe, Tokyo (JP); Tomoyuki Naoi, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 16/065,222

(22) PCT Filed: Dec. 26, 2016

(86) PCT No.: PCT/JP2016/088751
§ 371 (c)(1),
(2) Date: Jun. 22, 2018

(87) PCT Pub. No.: WO2017/111172
PCT Pub. Date: Jun. 29, 2017

(65) Prior Publication Data
US 2019/0008975 A1    Jan. 10, 2019

(30) Foreign Application Priority Data

Dec. 25, 2015  (JP) .................... 2015-254113

(51) Int. Cl.
| | | |
|---|---|---|
| A61K 47/54 | (2017.01) | |
| A61K 48/00 | (2006.01) | |
| A61K 31/397 | (2006.01) | |
| A61K 31/40 | (2006.01) | |
| C07D 205/04 | (2006.01) | |
| C12N 15/113 | (2010.01) | |
| A61K 9/00 | (2006.01) | |
| A61K 31/7105 | (2006.01) | |
| A61P 35/00 | (2006.01) | |

(52) U.S. Cl.
CPC .......... A61K 47/543 (2017.08); A61K 9/0019 (2013.01); A61K 31/397 (2013.01); A61K 31/40 (2013.01); A61K 31/7105 (2013.01); A61K 47/545 (2017.08); A61K 48/00 (2013.01); C07D 205/04 (2013.01); C12N 15/113 (2013.01); A61P 35/00 (2018.01)

(58) Field of Classification Search
None
See application file for complete search history.

(56) References Cited

U.S. PATENT DOCUMENTS

| | | |
|---|---|---|
| 2011/0256175 A1 | 10/2011 | Hope et al. |
| 2011/0311582 A1 | 12/2011 | Manoharan et al. |
| 2011/0311583 A1 | 12/2011 | Manoharan et al. |
| 2012/0027796 A1 | 2/2012 | Manoharan et al. |
| 2012/0095075 A1 | 4/2012 | Manoharan et al. |
| 2014/0308304 A1 | 10/2014 | Manoharan et al. |
| 2015/0057373 A1 | 2/2015 | Stanton et al. |
| 2015/0141678 A1 | 5/2015 | Payne et al. |
| 2015/0174261 A1 | 6/2015 | Kuboyama et al. |
| 2015/0239834 A1 | 8/2015 | Payne et al. |
| 2015/0239926 A1 | 8/2015 | Payne et al. |
| 2015/0265708 A1 | 9/2015 | Manoharan et al. |
| 2016/0095924 A1 | 4/2016 | Hope et al. |
| 2016/0199485 A1 | 7/2016 | Manoharan et al. |
| 2016/0213785 A1 | 7/2016 | Manoharan et al. |
| 2016/0244761 A1 | 8/2016 | Payne et al. |
| 2017/0001947 A1 | 1/2017 | Stanton et al. |
| 2017/0224619 A1 | 8/2017 | Hosoe et al. |
| 2018/0043009 A1 | 2/2018 | Manoharan et al. |
| 2018/0064807 A1 | 3/2018 | Manoharan et al. |
| 2018/0092971 A1 | 4/2018 | Manoharan et al. |
| 2018/0125985 A1 | 5/2018 | Manoharan et al. |
| 2019/0167800 A1 | 6/2019 | Manoharan et al. |

FOREIGN PATENT DOCUMENTS

| | | | |
|---|---|---|---|
| EP | 3 521 270 | 8/2019 | |
| TW | 201815736 | 5/2018 | |
| WO | 2010/042877 | 4/2010 | |
| WO | 2010/054401 | 5/2010 | |
| WO | 2011/090965 | 7/2011 | |
| WO | 2012/108397 | 8/2012 | |
| WO | 2013/086373 | 6/2013 | |
| WO | 2013/116126 | 8/2013 | |
| WO | WO 2013/116126 A1 * | 8/2013 | ............ A61K 45/00 |
| WO | 2013/0148541 | 10/2013 | |
| WO | 2014/007398 | 1/2014 | |
| WO | 2015/074085 | 5/2015 | |
| WO | 2016/002753 | 1/2016 | |

OTHER PUBLICATIONS

Maier et al., "Biodegradable Lipids Enabling Rapidly Eliminated Lipid Nanoparticles for Systemic Delivery of RNAi Therapeutics", Molecular Therapy, 2013, vol. 21, No. 8, pp. 1570-1578.

* cited by examiner

*Primary Examiner* — Brian J Davis

(74) *Attorney, Agent, or Firm* — Wenderoth, Lind & Ponack, L.L.P.

(57) ABSTRACT

The present invention provides a compound represented by formula (I) or a pharmaceutically acceptable salt thereof as a cationic lipid, and the like.

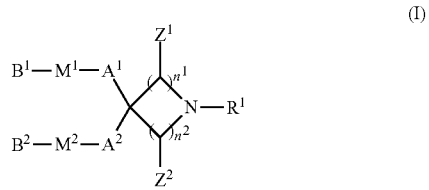

(I)

15 Claims, 2 Drawing Sheets
Specification includes a Sequence Listing.

[Figure 1]
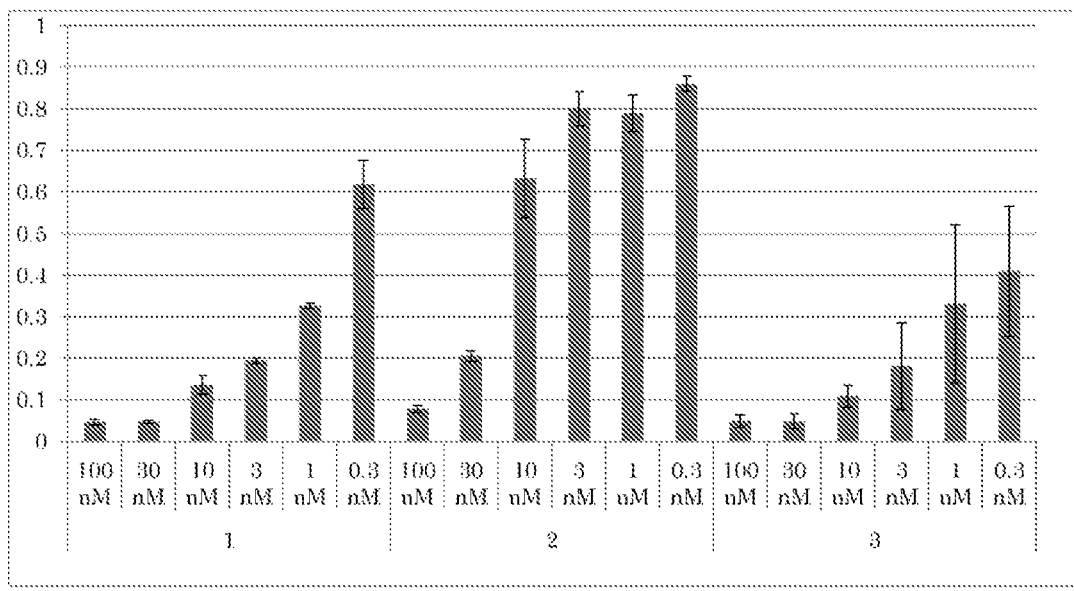
[Figure 2]
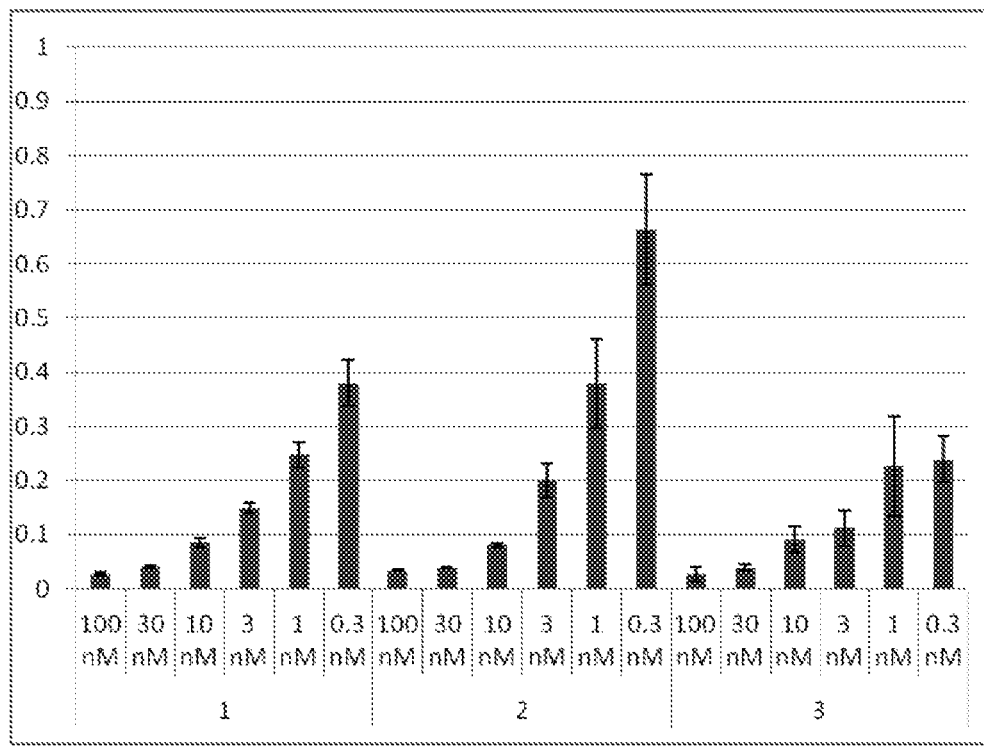

[Figure 3]
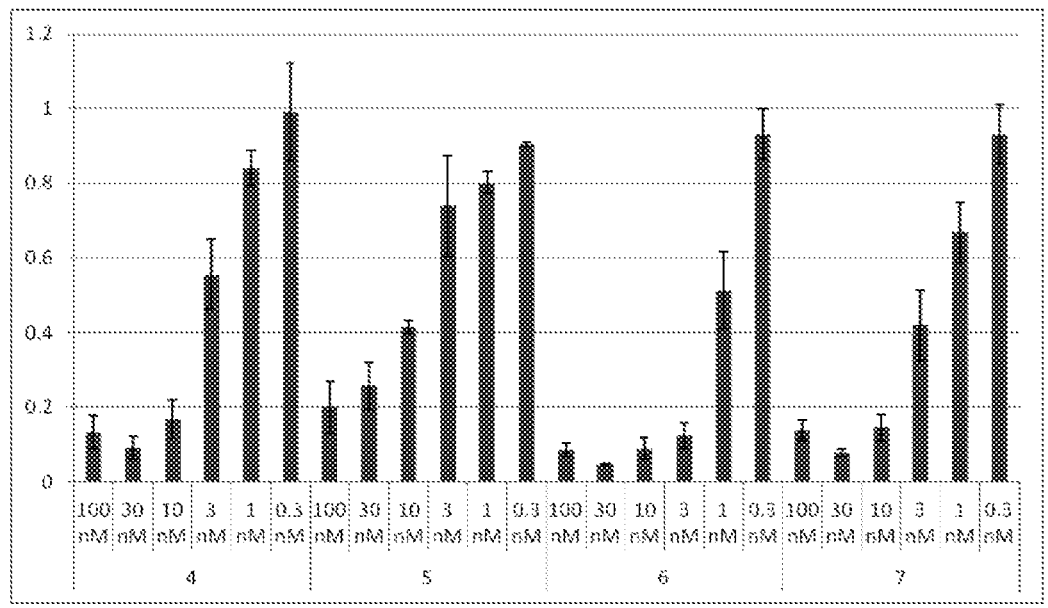
[Figure 4]
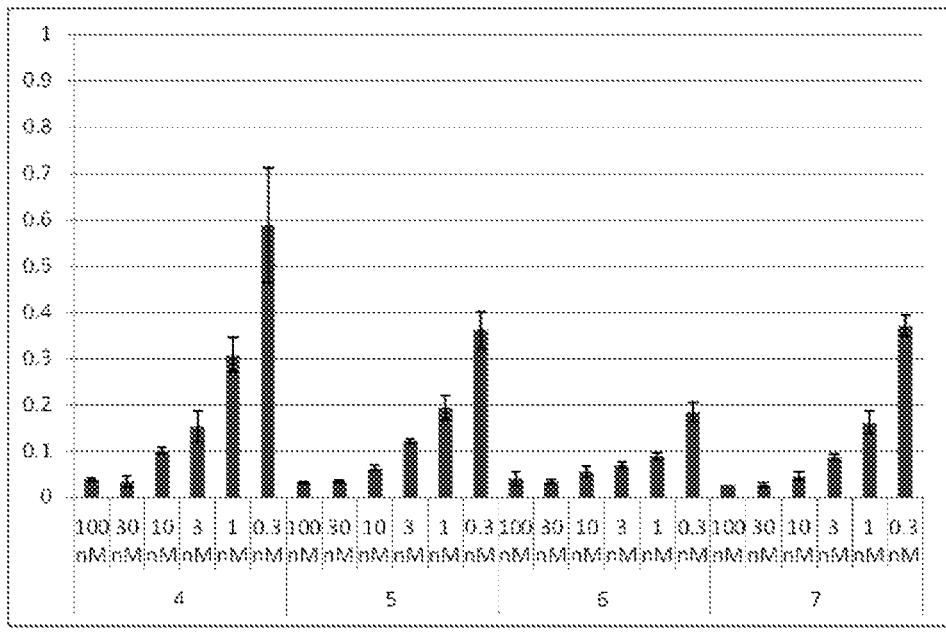

COMPOUND AS CATIONIC LIPID

TECHNICAL FIELD

The present invention relates to a novel compound as a cationic lipid, a composition containing the novel compound, and the like.

BACKGROUND ART

Cationic lipids are amphipathic molecules having a lipophilic region containing one or more hydrocarbon groups, and a hydrophilic region containing at least one positively charged polar head group. Cationic lipids are useful, because cationic lipids facilitate entry of macromolecules such as nucleic acids into the cytoplasm through the cell membrane by forming a positively charged (total charge) complex with macromolecules such as nucleic acids. This process, performed in vitro and in vivo, is known as transfection.

Patent Literatures 1 to 4 disclose cationic lipids and lipid particles containing the lipids, which are advantageous for delivering nucleic acids to cells in vivo, and for using nucleic acid-lipid particle compositions suitable for treatment of a disease.

Patent Literature 1 discloses cationic lipids, for example,

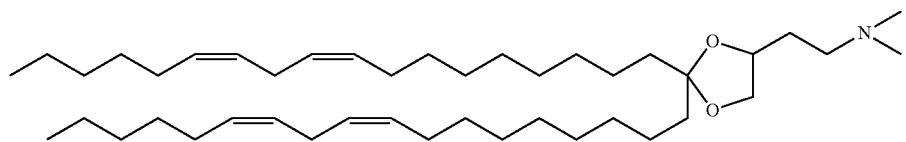 [SMILES: CCCCC/C=C\C/C=C\CCCCCCCCC1(CCCCCCCC/C=C\C/C=C\CCCCC)OCC(CCN(C)C)O1]

2,2-dilinoleyl-4-(2-dimethylaminoethyl)-[1,3]-dioxolane (DLin-KC2-DMA), and the like. Patent Literature 2 discloses cationic lipids, for example,

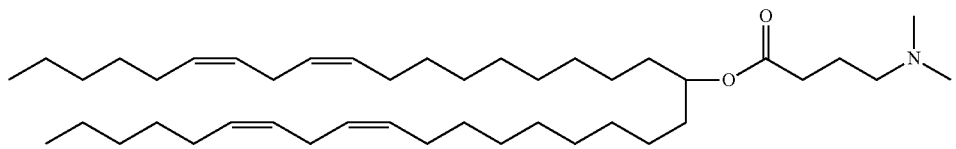 [SMILES: CCCCC/C=C\C/C=C\CCCCCCCCC(CCCCCCCC/C=C\C/C=C\CCCCC)OC(=O)CCCN(C)C]

(6Z,9Z,28Z,31Z)-heptatriaconta-6,9,28,31-tetraen-19-yl 4-(dimethylamino)butanoate (DLin-MC3-DMA), and the like. Patent Literature 3 discloses cationic lipids, for example,

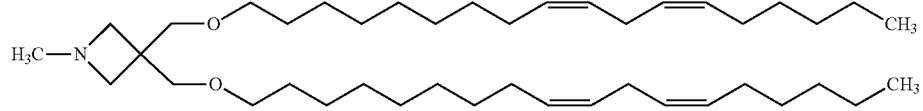 [SMILES: CCCCC/C=C\C/C=C\CCCCCCCCOCC1(COCCCCCCCC/C=C\C/C=C\CCCCC)CN(C)C1]

1-methyl-3,3-bis{[(9Z,12Z)-octadeca-9,12-dien-1-yloxy]methyl}azetidine, and the like. Patent Literature 4 discloses cationic lipids, for example,

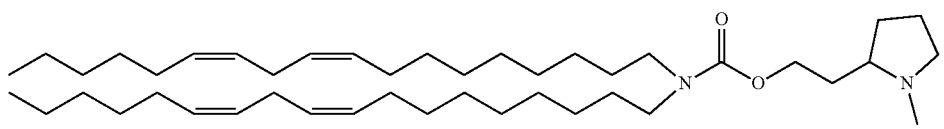 [SMILES: CCCCC/C=C\C/C=C\CCCCCCCCN(CCCCCCCC/C=C\C/C=C\CCCCC)C(=O)OCCC1CCCN1C]

2-(1-methylpyrrolidin-2-yl)ethyl di[(9Z,12Z)-octadeca-9,12-dienyl]carbamate, and the like.

Non Patent Literature 1 discloses that biodegradable groups are introduced to some lipid chains of cationic lipids so that the liver toxicity can be reduced while the ability to deliver nucleic acids to cells in vivo is maintained, and discloses, cationic lipids, for example,

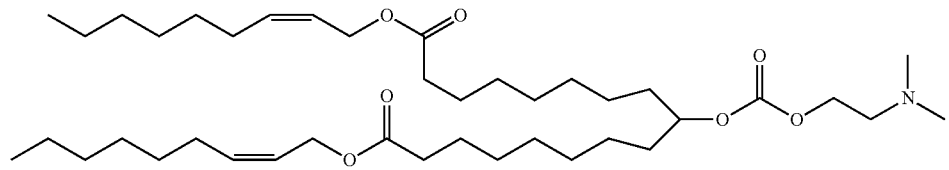 [SMILES: CCCCCC/C=C\COC(=O)CCCCCCCC(CCCCCCCC(=O)OC/C=C\CCCCCC)OC(=O)OCCN(C)C]

di[(Z)-non-2-en-1-yl]9-{[4-(dimethylamino)butanoyl]oxy}heptadecanedioate, and the like.

CITATION LIST

Patent Literature

Patent Literature 1: WO 2010/042877
Patent Literature 2: WO 2010/054401
Patent Literature 3: WO 2012/108397
Patent Literature 4: WO 2014/007398

Non Patent Literature

Non Patent Literature 1: Molecular Therapy, 2013, Vol. 21, p. 1570-1578

SUMMARY OF INVENTION

Technical Problem

An object of the present invention is to provide a novel compound as a cationic lipid that can introduce a nucleic acid, for example, into a cell, a composition containing the novel compound, and the like.

Means for Solving the Problems

The present invention relates to following (1) to (30):
(1) A compound represented by formula (I):

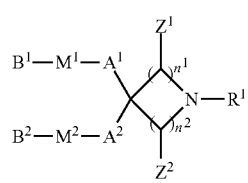

wherein $R^1$ is a hydrogen atom, C1-C3 alkyl, hydroxyC2-C4 alkyl, di-C1-C3 alkylaminoC2-C4 alkyl, formula (A):

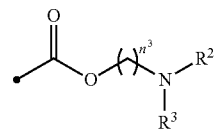

wherein $R^2$ and $R^3$ are, the same or different, a hydrogen atom or C1-C3 alkyl, or $R^2$ and $R^3$, together with the nitrogen atom to which they are attached, may form a C2-C6 nitrogen-containing heterocycle, and $n^3$ is an integer from 2 to 6, or
formula (B):

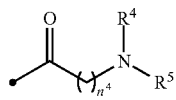

wherein $R^4$ and $R^5$ are, the same or different, a hydrogen atom or C1-C3 alkyl, or $R^4$ and $R^5$, together with the nitrogen atom to which they are attached, may form a C2-C6 nitrogen-containing heterocycle, and $n^4$ is an integer from 1 to 6;
$n^1$ is an integer from 0 to 4; $n^2$ is an integer from 1 to 4, provided that the case where $n^1$ is 0 and $n^2$ is 1 is excluded;
$Z^1$ is, independently for each carbon atom bonded thereto, a hydrogen atom or C1-C3 alkyl;
$Z^2$ is, independently for each carbon atom bonded thereto, a hydrogen atom or C1-C3 alkyl;
$A^1$ and $A^2$ are, the same or different, linear or branched C8-C20 alkylene or C8-C20 alkenylene, or C6-C18 alkyleneoxyC1-C3 alkylene or C6-C18 alkenyleneoxyC1-C3 alkylene;
$M^1$ and $M^2$ are, the same or different, selected from the group consisting of —OC(O)—, —C(O)O—, —SC(O)—, —C(O)S—, —OC(S)—, —C(S)O—, —SS—, —C($R^6$)=N—, —N=C($R^6$)—, —C($R^6$)=N—O—, —O—N=C($R^6$)—, —N($R^6$)C(O)—, —C(O)N($R^6$)—, —N($R^6$)C(S)—, —C(S)N($R^6$)—, —N($R^6$)C(O)N($R^7$)—, —N($R^6$)C(O)O—, —OC(O)N($R^6$)—, and —OC(O)O—;
$R^6$ and $R^7$ are, the same or different, a hydrogen atom or C1-C4 alkyl; and
$B^1$ and $B^2$ are, the same or different, linear or branched C1-C16 alkyl or C2-C16 alkenyl or a pharmaceutically acceptable salt thereof (cationic lipid).

(2) The compound according to the above described (1) or a pharmaceutically acceptable salt thereof (cationic lipid), wherein $M^1$ and $M^2$ are, the same or different, selected from the group consisting of —OC(O)—, —C(O)O—, —N($R^6$)C(O)—, and —C(O)N($R^6$)—.
(3) The compound according to the above described (2) or a pharmaceutically acceptable salt thereof (cationic lipid), wherein $M^1$ and $M^2$ are, the same or different, —OC(O)— or —C(O)O—.
(4) The compound according to any of the above described (1) to (3) or a pharmaceutically acceptable salt thereof (cationic lipid), wherein $A^1$ and $A^2$ are, the same or different, linear or branched C8-C20 alkylene or C8-C20 alkenylene.
(5) The compound according to any of the above described (1) to (4) or a pharmaceutically acceptable salt thereof (cationic lipid), wherein $B^1$-$M^1$-$A^1$- and $B^2$-$M^2$-$A^2$- are the same.
(6) The compound according to any of the above described (1) to (5) or a pharmaceutically acceptable salt thereof (cationic lipid), wherein $R^1$ is C1-C3 alkyl.
(7) The compound according to any of the above described (1) to (6) or a pharmaceutically acceptable salt thereof (cationic lipid), wherein $n^1$ is 1, and $n^2$ is an integer from 1 to 3.
(8) The compound according to any of the above described (1) to (7) or a pharmaceutically acceptable salt thereof (cationic lipid), wherein both of $n^1$ and $n^2$ are 1.
(9) A composition comprising the compound according to any of the above described (1) to (8) or a pharmaceutically acceptable salt thereof (cationic lipid) and a nucleic acid.
(10) The composition according to the above described (9), further comprising a neutral lipid and/or a polymer.
(11) The composition according to the above described (9) or (10), wherein the compound or the pharmaceutically acceptable salt thereof (cationic lipid) and the nucleic acid form a complex, or the compound or the pharmaceutically acceptable salt thereof (cationic lipid) combined with a neutral lipid and/or a polymer and the nucleic acid form a complex.
(12) The composition according to the above described (11), wherein the composition contains a lipid membrane with which the complex is enclosed.
(13) The composition according to any of the above described (9) to (12), wherein the nucleic acid is a nucleic acid having a silencing effect on a target gene through the use of RNA interference (RNAi)
(14) The composition according to the above described (13), wherein the target gene is a gene expressed in the liver, the lung, the kidney, the digestive tract, the central nervous system, or the spleen.
(15) The composition according to any of the above described (9) to (14), wherein the composition is for intravenous administration.
(16) A method for introducing a nucleic acid into a cell using the composition according to any of the above described (9) to (15).
(17) The method according to the above described (16), wherein the cell is a cell that resides in the liver, the lung, the kidney, the digestive tract, the central nervous system, or the spleen of a mammal.
(18) The method according to the above described (16) or (17), wherein the nucleic acid is introduced into a cell by the intravenous administration of the composition.
(19) A method for treating a disease related to the liver, the lung, the kidney, the digestive tract, the central nervous system, or the spleen, comprising the step of administering the composition according to any of the above described (9) to (15) to a mammal.
(20) The method according to the above described (19), wherein the administration is intravenous administration.
(21) A medicament comprising the composition according to any of the above described (9) to (15).
(22) A medicament for use in the treatment of a disease, comprising the composition according to any of the above described (9) to (15).
(23) The medicament according to the above described (22), wherein the disease is a disease related to the liver, the lung, the kidney, the digestive tract, the central nervous system, or the spleen.
(24) The medicament according to any of the above described (21) to (23), wherein the medicament is for intravenous administration.
(25) A therapeutic agent for a disease related to the liver, the lung, the kidney, the digestive tract, the central nervous system, or the spleen, comprising the composition according to any of the above described (9) to (15).
(26) The therapeutic agent for the liver, the lung, the kidney, the digestive tract, the central nervous system, or the spleen according to the above described (25), wherein the therapeutic agent is for intravenous administration.
(27) A method for treating a disease related to the liver, the lung, the kidney, the digestive tract, the central nervous system, or the spleen, comprising administering the composition according to any of the above described (9) to (15) to a patient in need thereof.
(28) The method according to the above described (27), wherein the administration is intravenous administration.
(29) The composition according to any of the above described (9) to (15), wherein the composition is for the treatment of a disease related to the liver, the lung, the kidney, the digestive tract, the central nervous system, or the spleen.
(30) The composition according to the above described (29), wherein the composition is for intravenous administration.

Advantage of Invention

The present invention can provide a novel compound as a cationic lipid that can introduce a nucleic acid, for example, into a cell, a composition containing the novel compound, and the like.

BRIEF DESCRIPTION OF THE DRAWINGS

FIG. 1 shows that the expression level of HPRT1 mRNA was evaluated by semi-quantitative RT-PCR measurement when a human pancreatic cancer cell line MIA-PaCa2 was treated with each of the preparations 1 to 3 (compositions containing the compounds 1 to 3, respectively) obtained in Examples 5 and 6. The mRNA level of a specimen was calculated as a relative ratio of a calculated HPRT1 mRNA level with respect to a GAPDH mRNA level with the value in a negative control treatment group defined as 1. The ordinate depicts the relative value of the mRNA level of the specimen thus calculated. The abscissa depicts preparation No. and a siRNA concentration (nM) in the preparations.
FIG. 2 shows that the expression level of HPRT1 mRNA was evaluated by semi-quantitative RT-PCR measurement when a human lung cancer cell line NCI-H358 was treated with each of the preparations 1 to 3 (compositions containing the compounds 1 to 3, respectively) obtained in Examples 5 and 6. The mRNA level of a specimen was calculated as a relative ratio of a calculated HPRT1 mRNA level with respect to a GAPDH mRNA level with the value in a negative control treatment group defined as 1. The ordinate depicts the relative value of the mRNA level of the specimen thus calculated. The abscissa depicts preparation No. and a siRNA concentration (nM) in the preparations.

FIG. 3 shows that the expression level of HPRT1 mRNA was evaluated by semi-quantitative RT-PCR measurement when a human pancreatic cancer cell line MIA-PaCa2 was treated with each of the preparations 4 to 8 (compositions containing the compounds 1 to 4, respectively) obtained in Examples 7 and 8. The mRNA level of a specimen was calculated as a relative ratio of a calculated HPRT1 mRNA level with respect to a GAPDH mRNA level with the value in a negative control treatment group defined as 1. The ordinate depicts the relative value of the mRNA level of the specimen thus calculated. The abscissa depicts preparation No. and a siRNA concentration (nM) in the preparations.

FIG. 4 shows that the expression level of HPRT1 mRNA was evaluated by semi-quantitative RT-PCR measurement when a human lung cancer cell line NCI-H358 was treated with each of the preparations 4 to 8 (compositions containing the compounds 1 to 4, respectively) obtained in Examples 7 and 8. The mRNA level of a specimen was calculated as a relative ratio of a calculated HPRT1 mRNA level with respect to a GAPDH mRNA level with the value in a negative control treatment group defined as 1. The ordinate depicts the relative value of the mRNA level of the specimen thus calculated. The abscissa depicts preparation No. and a siRNA concentration (nM) in the preparations.

MODE FOR CARRYING OUT THE INVENTION

The compound of the present invention is a compound represented by formula (I):

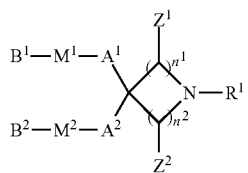

(I)

wherein $R^1$ is a hydrogen atom, C1-C3 alkyl, hydroxyC2-C4 alkyl, di-C1-C3 alkylamino-C2-C4 alkyl, formula (A):

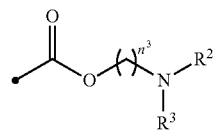

(A)

wherein $R^2$ and $R^3$ are, the same or different, a hydrogen atom or C1-C3 alkyl, or $R^2$ and $R^3$, together with the nitrogen atom to which they are attached, may form a C2-C6 nitrogen-containing heterocycle, and $n^3$ is an integer from 2 to 6, or formula (B):

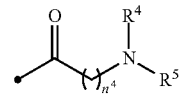

(B)

wherein $R^4$ and $R^5$ are, the same or different, a hydrogen atom or C1-C3 alkyl, or $R^4$ and $R^5$, together with the nitrogen atom to which they are attached, may form a C2-C6 nitrogen-containing heterocycle, and $n^4$ is an integer from 1 to 6;

$n^1$ is an integer from 0 to 4; $n^2$ is an integer from 1 to 4, provided that the case where $n^1$ is 0 and $n^2$ is 1 is excluded;

$Z^1$ is, independently for each carbon atom bonded thereto, a hydrogen atom or C1-C3 alkyl;

$Z^2$ is, independently for each carbon atom bonded thereto, a hydrogen atom or C1-C3 alkyl;

$A^1$ and $A^2$ are, the same or different, linear or branched C8-C20 alkylene or C8-C20 alkenylene, or C6-C18 alkyleneoxyC1-C3 alkylene or C6-C18 alkenyleneoxyC1-C3 alkylene;

$M^1$ and $M^2$ are, the same or different, selected from the group consisting of —OC(O)—, —C(O)O—, —SC(O)—, —C(O)S—, —OC(S)—, —C(S)O—, —SS—, —C($R^6$)=N—, —N=C($R^6$)—, —C($R^6$)=N—O—, —O—N=C($R^6$)—, —N($R^6$)C(O)—, —C(O)N($R^6$)—, —N($R^6$)C(S)—, —C(S)N($R^6$)—, —N($R^6$)C(O)N($R^7$)—, —N($R^6$)C(O)O—, —OC(O)N($R^6$)—, and —OC(O)O—;

$R^6$ and $R^7$ are, the same or different, a hydrogen atom or C1-C4 alkyl; and $B^1$ and $B^2$ are, the same or different, linear or branched C1-C16 alkyl or C2-C16 alkenyl.

The compound represented by formula (I) has a lipophilic region containing two hydrocarbon groups, and a hydrophilic region containing one positively chargeable polar head group, and has properties as a cationic lipid.

Hereinafter, the compound represented by formula (I) is also referred to as compound (I). The same holds true for compounds of other formula numbers. Hereinafter, the compound represented by formula (I) or a pharmaceutically acceptable salt thereof is also collectively referred to as a "cationic lipid".

Examples of the C1-C3 alkyl include methyl, ethyl, propyl, isopropyl, cyclopropyl, or the like.

In the present invention, when C1-C3 alkyl is taken as an example, C1-C3 of the C1-C3 alkyl means that the number of carbon atoms is 1 to 3.

The hydroxyC2-C4 alkyl means that any carbon atom of C2-C4 alkyl is substituted with hydroxy. Examples of the C2-C4 alkyl moiety include ethyl, propyl, butyl, or the like.

The di-C1-C3 alkylamino-C2-C4 alkyl means that any carbon atom of C2-C4 alkyl is substituted with di-C1-C3 alkylamino. Examples of the C2-C4 alkyl moiety include ethyl, propyl, butyl, or the like.

Examples of the C1-C3 alkyl moieties in di-C1-C3 alkylamino include methyl, ethyl, propyl, isopropyl, cyclopropyl, or the like. The two C1-C3 alkyl moieties may be the same or different.

Examples of the C2-C6 nitrogen-containing heterocycle include an aziridine ring, an azetidine ring, a pyrrolidine ring, a piperidine ring, an azepane ring, or the like. The C2-C6 nitrogen-containing heterocycle may be substituted with 1 to 3, same or different, C1-C3 alkyl groups (as defined above), hydroxy, methoxy, or the like.

Examples of the linear or branched C8-C20 alkylene include octylene, nonylene, undecylene, tridecylene, tetradecylene, 2,6,10-trimethylundecylene, pentadecylene, 3,7,11-trimethyldodecylene, hexadecylene, heptadecylene, octadecylene, nonadecylene, 2,6,10,14-tetramethylpentadecylene, 3,7,11,15-tetramethylhexadecylene, or the like. The linear or branched C8-C20 alkylene is preferably nonylene, undecylene, tridecylene, or hexadecylene, more preferably nonylene or undecylene.

In the description about the linear or branched C8-C20 alkylene, when 2,6,10-trimethylundecylene is taken as an example, 2,6,10- which indicates the positions of substitution with substituents means that carbon atoms in $A^1$ and $A^2$ attached to the carbon atoms of the nitrogen-containing heterocycle are defined as positions 1.

The linear or branched C8-C20 alkenylene can be any group containing one or more double bonds in linear or branched C8-C20 alkylene. Examples thereof include (Z)-tetradec-9-enylene, (Z)-hexadec-9-enylene, (Z)-octadec-6-enylene, (Z)-octadec-9-enylene, (E)-octadec-9-enylene, (Z)-octadec-11-enylene, (9Z,12Z)-octadeca-9,12-dienylene, (9Z,12Z,15Z)-octadeca-9,12,15-trienylene, or the like. The linear or branched C8-C20 alkenylene is preferably (Z)-tetradec-9-enylene, (Z)-hexadec-9-enylene, (Z)-octadec-9-enylene, (Z)-octadec-11-enylene, or (9Z,12Z)-octadeca-9,12-dienylene.

In the description about the linear or branched C8-C20 alkenylene, when (Z)-tetradec-9-enylene is taken as an example, -9- which indicates the position of a double bond means that carbon atoms in $A^1$ and $A^2$ attached to the carbon atoms of the nitrogen-containing heterocycle are defined as positions 1.

Examples of the C1-C3 alkylene moiety in C6-C18 alkyleneoxyC1-C3 alkylene include methylene, ethylene, propylene, or the like.

Examples of the C6-C18 alkylene moiety in C6-C18 alkyleneoxyC1-C3 alkylene include hexylene, heptylene, octylene, nonylene, decylene, undecylene, tridecylene, tetradecylene, 2,6,10-trimethylundecylene, pentadecylene, 3,7,11-trimethyldodecylene, hexadecylene, heptadecylene, octadecylene, or the like, and preferably include hexylene, heptylene, octylene, nonylene, and decylene.

Examples of the C1-C3 alkylene moiety in C6-C18 alkenyleneoxyC1-C3 alkylene include methylene, ethylene, and propylene. The C6-C18 alkenylene moiety can be any moiety containing one or more double bonds in the C6-C18 alkylene moiety in C6-C18 alkyleneoxyC1-C3 alkylene. Examples thereof include (Z)-tetradec-9-enyl, (Z)-hexadec-9-enyl, (Z)-octadec-6-enyl, (Z)-octadec-9-enyl, (E)-octadec-9-enyl, or the like. The C6-C18 alkenylene moiety is preferably (Z)-hexadec-9-enyl, (Z)-octadec-6-enyl, (Z)-octadec-9-enyl, (9Z,12Z)-octadeca-9,12-dienyl, (Z)-icos-11-enyl, or (11Z,14Z)-icosa-11,14-dienyl. The C1-C3 alkylene moiety constituting the C6-C18 alkyleneoxyC1-C3 alkylene or the C6-C18 alkenyleneoxyC1-C3 alkylene is positioned on the nitrogen-containing heterocycle side in formula (I).

Examples of the C1-C4 alkyl include methyl, ethyl, propyl, isopropyl, cyclopropyl, butyl, iso-butyl, sec-butyl, tert-butyl, cyclobutyl, or the like.

Examples of the linear or branched C1-C16 alkyl include methyl, ethyl, propyl, isopropyl, butyl, tert-butyl, hexyl, octyl, nonyl, decyl, dodecyl, tetradecyl, 3,7,11-trimethyldodecyl, hexadecyl, or the like. The linear or branched C1-C16 alkyl is preferably octyl, nonyl, decyl, or dodecyl.

In the description about the linear or branched C1-C16 alkyl, when 3,7,11-trimethyldodecyl is taken as an example, 3,7,11- which indicates the positions of substitution with substituents means that carbon atoms in $B^1$ and $B^2$ attached to $M^1$ and $M^2$ are defined as positions 1.

The linear or branched C2-C16 alkenyl can be any group containing one or more double bonds in linear or branched C2-C16 alkyl of the linear or branched C1-C16 alkyl. Examples thereof include (Z)-but-2-enyl, (Z)-pent-2-enyl, (Z)-hex-2-enyl, (Z)-hept-2-enyl, (Z)-oct-2-enyl, (Z)-non-2-enyl, (Z)-non-3-enyl, (E)-non-2-enyl, non-8-enyl, (Z)-dodec-2-enyl, (Z)-dodec-2-enyl, (Z)-tridec-2-enyl, or the like. The linear or branched C2-C16 alkenyl is preferably (Z)-hept-2-enyl, (Z)-non-2-enyl, (Z)-non-3-enyl, non-8-enyl, (Z)-dodec-2-enyl, or (Z)-tridec-2-enyl.

In the description about the linear or branched C2-C16 alkenyl, when (Z)-but-2-ene is taken as an example, -2- which indicates the position of substitution with a substituent means that carbon atoms in $B^1$ and $B^2$ attached to $M^1$ and $M^2$ are defined as positions 1.

In the present invention, a group having a cyclopropane ring formed by adding formally a methylene biradical to a double bond of the linear or branched C8-C20 alkenylene is also included in the linear or branched C8-C20 alkenylene. The same holds true for the C6-C18 alkenylene moiety in C6-C18 alkenyleneoxyC1-C3 alkylene, and the linear or branched C2-C16 alkenyl.

When (Z)-non-2-ene is taken as an example, the following group having a cyclopropane ring is also included in the linear or branched C8-C20 alkenylene according to the present invention:

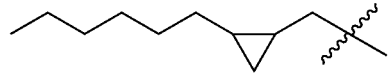 [SMILES: *CC1CC1CCCCCC]

$A^1$ and $A^2$ are, the same or different, preferably linear or branched C8-C20 alkylene or C8-C20 alkenylene and are, the same or different, preferably linear C8-C20 alkylene. $A^1$ and $A^2$ are preferably the same and linear or branched C8-C20 alkylene or C8-C20 alkenylene, more preferably the same and linear C8-C20 alkylene.

$M^1$ and $M^2$ are, the same or different, preferably —OC(O)—, —C(O)O—, —C(S)O—, —SS—, —N(R$^6$)C(O)—, —C(O)N(R$^6$)—, —C(S)(NR$^6$)—, —N(R$^6$)C(O)N(R$^7$)—, —N(R$^6$)C(O)O—, —OC(O)N(R$^6$)—, or —OC(O)O—, more preferably —OC(O)—, —C(O)O—, —N(R$^6$)C(O)—, —C(O)N(R$^6$)—, —N(R$^6$)C(O)N(R$^7$)—, —N(R$^6$)C(O)O—, —OC(O)N(R$^6$)—, or —OC(O)O—, further preferably —OC(O)—, —C(O)O—, —N(R$^6$)C(O)—, or —C(O)N(R$^6$)—, still further preferably —OC(O)— or —C(O)O—.

In the description about $M^1$ and $M^2$, when the case where each of $M^1$ and $M^2$ is —OC(O)— is taken as an example, —OC(O)— means being bonded as $B^1$—OC(O)-$A^1$ or $B^2$—OC(O)-$A^2$.

$R^6$ and $R^7$ are, the same or different, preferably a hydrogen atom, methyl, or ethyl, more preferably the same or different and a hydrogen atom or methyl, further preferably the same and a hydrogen atom or methyl, still further preferably a hydrogen atom.

$B^1$ and $B^2$ are, the same or different, preferably linear C1-C16 alkyl or C2-C16 alkenyl, more preferably the same and linear C1-C16 alkyl or C2-C16 alkenyl, further preferably the same and linear C2-C16 alkenyl.

Preferably, $B^1$-$M^1$-$A^1$ and $B^2$-$M^2$-$A^2$ are the same. $B^1$-$M^1$-$A^1$ and $B^2$-$M^2$-$A^2$ are, the same or different, preferably any of the following structures (1) to (11), more preferably the same and any of the following structures (1) to (11), further preferably any of the following structures (1) to (4):

n⁵ is preferably an integer from 1 to 10, more preferably an integer from 1 to 5, further preferably an integer from 2 to 4, still further preferably 2 or 4.

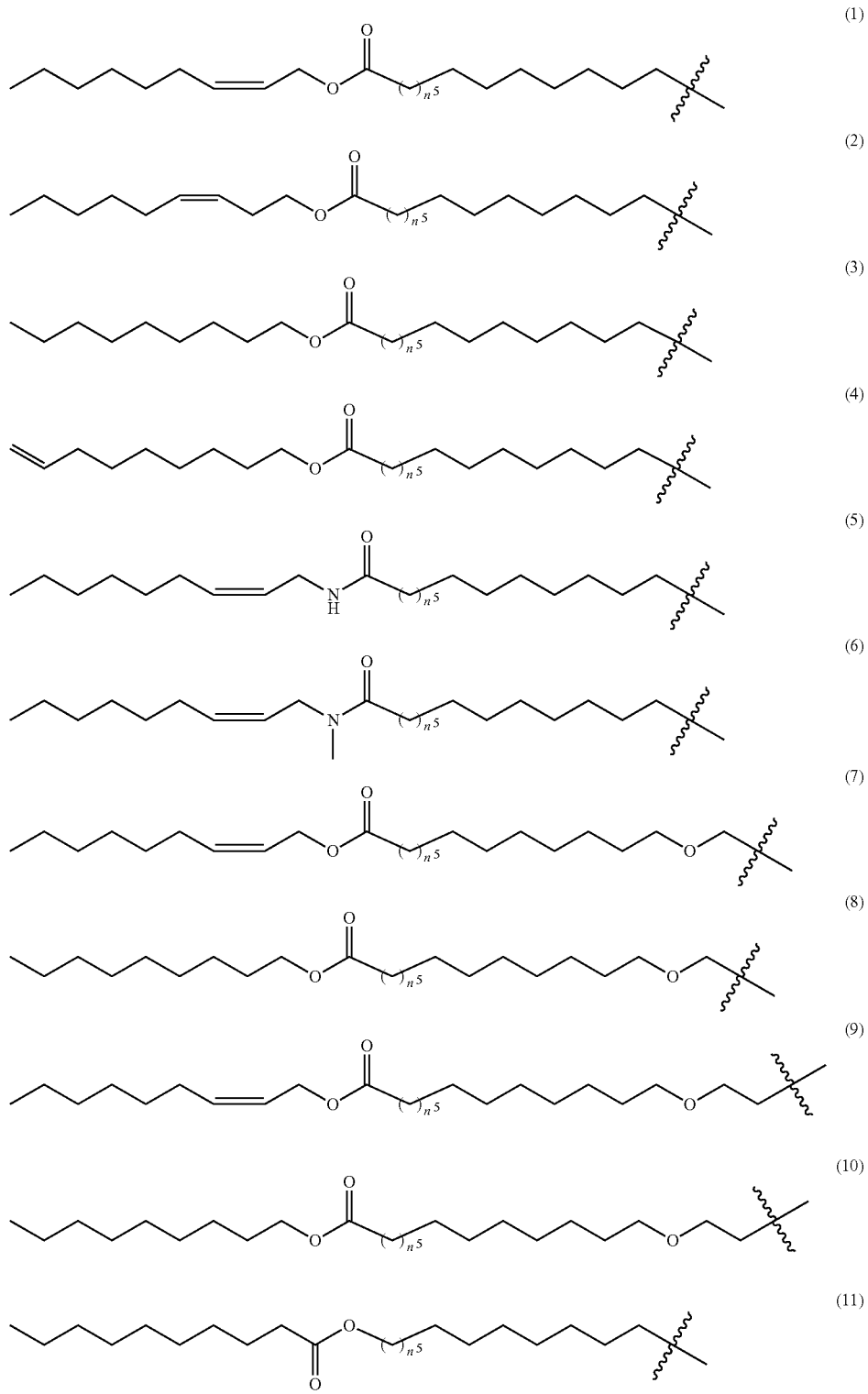

In the above described structures (1) to (11), the bond represented by a wavy line is a bond to a carbon atom of the nitrogen-containing heterocycle in formula (I).

$R^1$ is preferably C1-C3 alkyl, the above formula (A), or the above formula (B), more preferably C1-C3 alkyl or the above formula (A), further preferably C1-C3 alkyl.

When $R^1$ is C1-C3 alkyl, $R^1$ is preferably methyl, ethyl, propyl, or cyclopropyl, more preferably methyl or ethyl, further preferably methyl.

When $R^1$ is formula (A), $R^2$ and $R^3$ are, the same or different, preferably a hydrogen atom or C1-C3 alkyl.

When $R^1$ is formula (B), $R^4$ and $R^5$ are, the same or different, preferably a hydrogen atom or C1-C3 alkyl.

When $R^2$ and $R^3$, together with the nitrogen atom to which they are attached, form a C2-C6 nitrogen-containing heterocycle, $R^2$ and $R^3$, together with the nitrogen atom to which they are attached, are preferably an azetidine ring, a pyrrolidine ring, a piperidine ring, or an azepane ring, more preferably a pyrrolidine ring or a piperidine ring.

When $R^2$ and $R^3$ are, the same or different, C1-C3 alkyl, $R^3$ is preferably methyl or ethyl, more preferably methyl.

Preferably, $R^2$ and $R^3$ are the same and methyl.

$n^3$ is preferably an integer from 2 to 4, more preferably 3.

When $R^4$ and $R^5$, together with the nitrogen atom to which they are attached, form a C2-C6 nitrogen-containing heterocycle, $R^4$ and $R^5$, together with the nitrogen atom to which they are attached, are preferably a pyrrolidine ring or a piperidine ring.

When $R^4$ and $R^5$ are, the same or different, C1-C3 alkyl, $R^4$ and $R^5$ are preferably methyl or ethyl, more preferably methyl.

Preferably, $R^4$ and $R^5$ are the same and methyl.

$n^4$ is preferably an integer from 2 to 4, more preferably 3.

$n^1$ is preferably 1. When $n^1$ is 1, $n^2$ is preferably an integer from 1 to 3, more preferably 1 or 2, further preferably 1.

$Z^1$ is, independently for each carbon atom bonded thereto, preferably a hydrogen atom or methyl, more preferably a hydrogen atom.

$Z^2$ is, independently for each carbon atom bonded thereto, preferably a hydrogen atom or C1-C3 alkyl, more preferably a hydrogen atom or methyl, further preferably a hydrogen atom.

In the present invention, the term "independently for each carbon atom bonded thereto" means that when two or more $Z^1$ moieties are present in formula (I), these $Z^1$ moieties are the same or different and can each be selected from a hydrogen atom and C1-C3 alkyl, depending on the carbon atom bonded to each $Z^1$. For example, when two $Z^1$ moieties are present in formula (I), the term not only means that these $Z^1$ moieties are the same, but means that the case where one of the $Z^1$ moieties is a hydrogen atom and the other $Z^1$ moiety is C1-C3 alkyl or the case where the two $Z^1$ moieties are different C1-C3 alkyl groups is also included. The same holds true for the case where two or more $Z^2$ moieties are present in formula (I).

When both of $n^1$ and $n^2$ are 1, $Z^1$ and $Z^2$ are, the same or different, preferably a hydrogen atom or methyl. More preferably, $Z^1$ is a hydrogen atom or methyl, and $Z^2$ is a hydrogen atom. Further preferably, $Z^1$ and $Z^2$ are the same and a hydrogen atom.

Methods for producing the compound represented by formula (I) of the present invention or the pharmaceutically acceptable salt thereof (cationic lipid) will be described.

In the production methods shown below, if defined groups react under conditions of the production methods or are unsuitable for carrying out the production methods, the desired compounds can be produced by use of introduction and removal methods of protective groups commonly used in organic synthetic chemistry [e.g., methods described in Protective Groups in Organic Synthesis, third edition, T. W. Greene, John Wiley & Sons Inc. (1999) or the like] or the like. If necessary, the order of reaction steps including substituent introduction or the like may be changed.

Production Method 1

Compound (I) wherein both of $n^1$ and $n^2$ are 1, both of $Z^1$ and $Z^2$ are hydrogen atoms, $R^1$ is a hydrogen atom, C1-C3 alkyl, hydroxyC2-C4 alkyl, or di-C1-C3 alkylamino-C2-C4 alkyl, and $M^1$ and $M^2$ are the same and —OC(O)— (compound (Ia)) can be produced by, for example, a method given below.

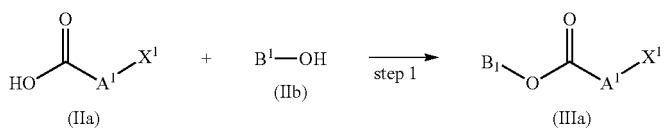

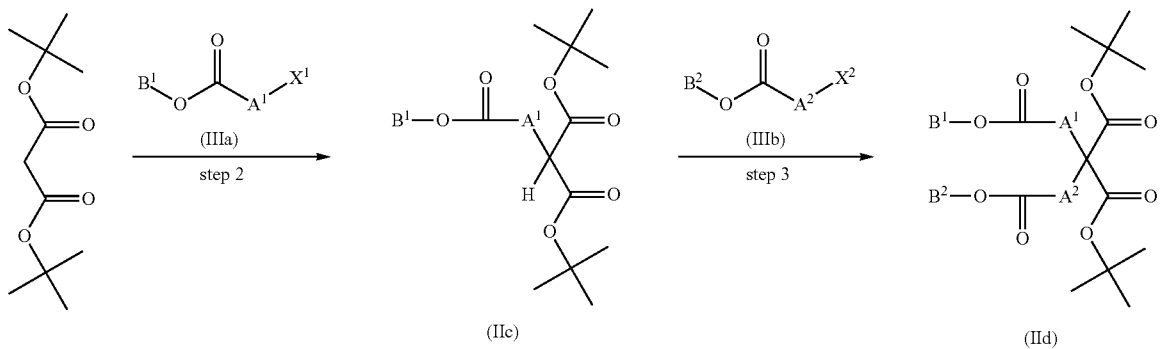

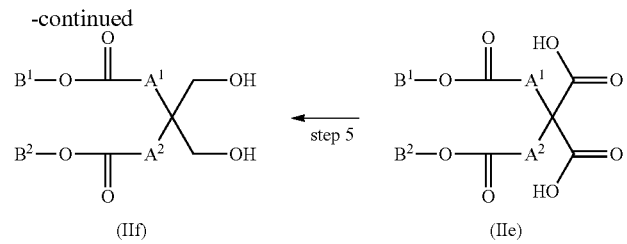

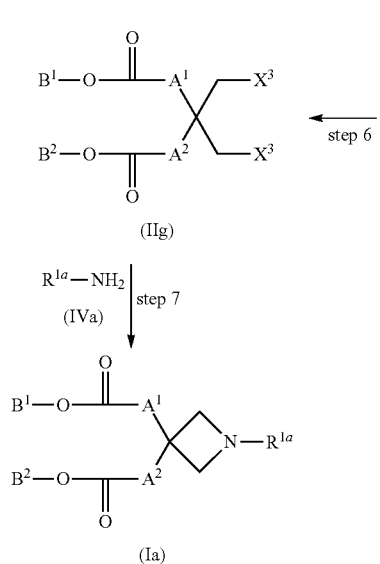

wherein $A^1$, $A^2$, $B^1$ and $B^2$ are each as defined above, $R^{1a}$ is a hydrogen atom, C1-C3 alkyl, hydroxyC2-C4 alkyl, or di-C1-C3 alkylamino-C2-C4 alkyl, $X^1$, $X^2$ and $X^3$ are, the same or different, a leaving group such as a chlorine atom, a bromine atom, an iodine atom, trifluoromethanesulfonyloxy, methanesulfonyloxy, benzenesulfonyloxy, or p-toluenesulfonyloxy.

Step 1

Compound (IIIa) can be produced by reacting compound (IIa) with compound (IIb) at room temperature to 200° C. for 5 minutes to 100 hours in the presence of 1 to 10 equivalents of a condensing agent and 1 to 10 equivalents of a base without a solvent or in a solvent.

Examples of the solvent include dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, N-methylpyrrolidone, pyridine, or the like. These solvents can be used singly or as a mixture.

Examples of the condensing agent include 1-ethyl-3-(3-dimethylaminopropyl)carbodiimide hydrochloride, N,N'-dicyclohexylcarbodiimide, 4-(4,6-dimethoxy-1,3,5-triazin-2-yl)-4-methylmorpholinium chloride n-hydrate, 1H-benzotriazol-1-yloxytris(dimethylamino)phosphonium hexafluorophosphate, O-(7-azabenzotriazol-1-yl)-N,N,N',N'-tetramethyluronium hexafluorophosphate, or the like.

Examples of the base include potassium carbonate, cesium carbonate, triethylamine, diisopropylethylamine, N-methylmorpholine, pyridine, or the like.

Compound (IIa) can be obtained as a commercially available product or by a method known in the art [e.g., "New Experimental Chemistry 14, Synthesis and Reaction of Organic Compound (II)", first edition, Maruzen Co., Ltd. (1977)) or a method equivalent thereto.

Compound (IIb) can be obtained as a commercially available product.

Steps 2 and 3

Compound (IIc) can be produced by reacting di-tert-butyl malonate with compound (IIIa) at room temperature to 200° C. for 5 minutes to 100 hours in the presence of 1 to 10 equivalents of a base without a solvent or in a solvent.

Compound (IId) can be produced by reacting compound (IIc) with compound (IIIb) at room temperature to 200° C. for 5 minutes to 100 hours in the presence of 1 to 10 equivalents of a base without a solvent or in a solvent.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, N-methylpyrrolidone, pyridine, or the like. These solvents can be used singly or as a mixture.

Examples of the base include potassium carbonate, cesium carbonate, sodium methoxide, potassium tert-butoxide, sodium hydride, triethylamine, diisopropylethylamine, N-methylmorpholine, pyridine, 1,8-diazabicyclo[5.4.0]-7-undecene (DBU), or the like.

When $A^1$ and $A^2$ are the same and $B^1$ and $B^2$ are the same, compound (IId) can be produced by using 2 equivalents or more of compound (IIIa) in step 2.

Di-tert-butyl malonate can be obtained as a commercially available product.

Compound (IIIb) can be produced in the same way as in compound (IIIa).

Step 4 Compound (IIe) can be produced by reacting compound (IId) with 5 to 100 equivalents of an acid at −78° C. to 100° C. for 5 minutes to 100 hours without a solvent or in a solvent.

Examples of the solvent include those listed in step 1.

Examples of the acid include trifluoroacetic acid, trichloroacetic acid, hydrochloric acid, sulfuric acid, hydrobromic acid, or the like.

Step 5

Compound (IIf) can be produced by reacting compound (IIe) with 4 equivalents to a large excess of a reducing agent at −20° C. to 150° C. for 5 minutes to 72 hours, if necessary in the presence of a catalytic amount to 10 equivalents of an additive, in a solvent. The catalytic amount refers to 0.01 equivalents to 0.5 equivalents.

Examples of the solvent include toluene, dichloromethane, diethyl ether, tetrahydrofuran, 1,2-dimethoxyethane, 1,4-dioxane, or the like. These solvents can be used singly or as a mixture.

Examples of the reducing agent include a borane-tetrahydrofuran complex, a borane-dimethyl sulfide complex, lithium aluminum hydride, lithium borohydride, lithium triacetoxyborohydride, diisobutyl aluminum hydride, sodium bis(2-methoxyethoxy)aluminum hydride, or the like.

Examples of the additive include aluminum chloride, cerium chloride, titanium tetrachloride, titanium tetraisopropoxide, or the like.

Step 6

Compound (IIg) can be produced by reacting compound (IIf) with 2 equivalents or more of a halogenation reagent or a pseudohalogenation reagent at −20° C. to 150° C. for 5 minutes to 100 hours in the presence of, if necessary, preferably 1 to 10 equivalents of a base and, if necessary, preferably 1 to 10 equivalents of an additive, without a solvent or in a solvent.

Examples of the solvent include those listed in step 5.

Examples of the halogenation reagent or the pseudohalogenation reagent include thionyl chloride, sulfuryl chloride, phosphorus trichloride, phosphorus pentachloride, phosphorus oxychloride, phosphorus tribromide, hydrogen bromide, hydrogen iodide, mesylic anhydride, mesyl chloride, tosylic anhydride, benzenesulfonyl chloride, benzenesulfonic anhydride, tosyl chloride, trifluoromethanesulfonic anhydride, or the like.

Examples of the base include pyridine, 2,6-lutidine, 2,4,6-collidine, triethylamine, N,N-diisopropylethylamine, or the like.

Examples of the additive include sodium chloride, sodium bromide, lithium bromide, lithium chloride, or the like.

Step 7

Compound (Ia) can be produced by reacting compound (IIf) with 1 equivalent to a large excess of compound (IVa) at room temperature to 200° C. for 5 minutes to 100 hours without a solvent or in a solvent.

Examples of the solvent include those listed in steps 2 and 3.

Compound (IVa) can be obtained as a commercially available product.

Production Method 2

Compound (I) wherein both of $n^1$ and $n^2$ are 1, both of $Z^1$ and $Z^2$ are hydrogen atoms, and $R^1$ is a hydrogen atom, C1-C3 alkyl, hydroxyC2-C4 alkyl, or di-C1-C3 alkylamino-C2-C4 alkyl (compound (Ia')) can be produced by, for example, a method given below.

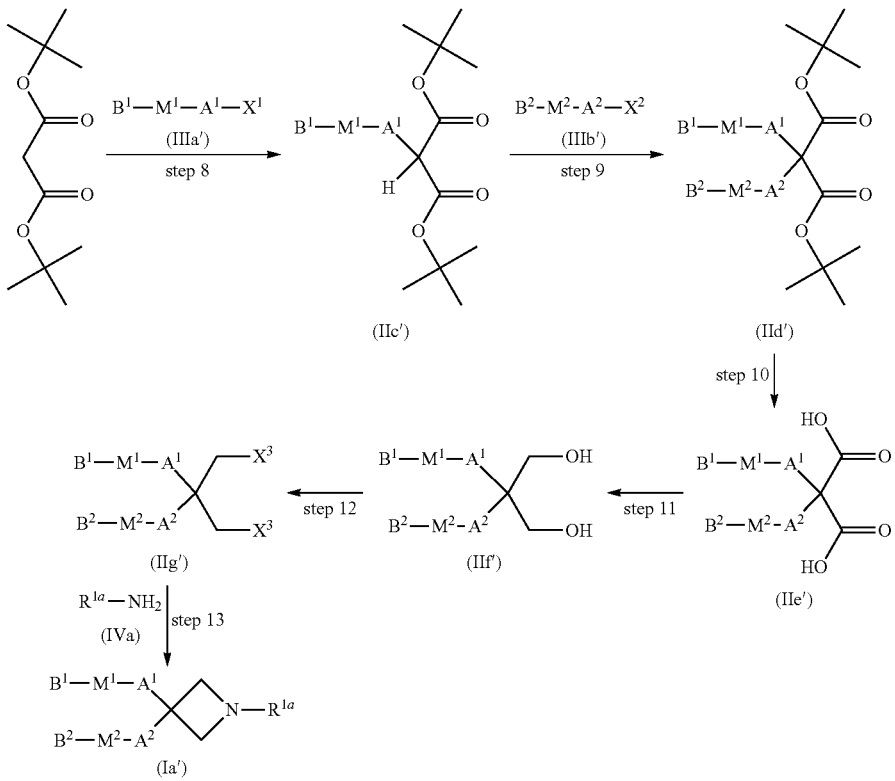

wherein $A^1$, $A^2$, $M^1$, $M^2$, $B^1$, $B^2$, $R^{1a}$, $X^1$, $X^2$ and $X^3$ are each as defined above.

Steps 8 and 9

Compound (IIc') can be produced in the same way as in step 2 by using compound (IIIa') instead of compound (IIIa).

Compound (IId') can be produced in the same way as in step 3 by using compounds (IIc') and (IIIb') instead of compounds (IIc) and (IIIb).

Compound (IIIa') and compound (IIIb') wherein each of $M^1$ and $M^2$ is —OC(O)— can be produced by the method shown in step 1 of Production method 1.

Compound (IIIa') and compound (IIIb') wherein each of $M^1$ and $M^2$ is a moiety other than —OC(O)— can be produced by using the corresponding starting materials.

Step 10

Compound (IIe') can be produced in the same way as in step 4 by using compound (IId') instead of compound (IId).

Step 11

Compound (IIf') can be produced in the same way as in step 5 by using compound (IIe') instead of compound (IIe).

Step 12

Compound (IIg') can be produced in the same way as in step 6 by using compound (IIf') instead of compound (IIf).

Step 13

Compound (Ia') can be produced in the same way as in step 7 by using compound (IIg') instead of compound (IIg).

Production Method 3

Compound (I) wherein both of $n^1$ and $n^2$ are 1, both of $Z^1$ and $Z^2$ are hydrogen atoms, and $R^3$ is formula (A) (compound (Ic)) can be produced by, for example, a method given below.

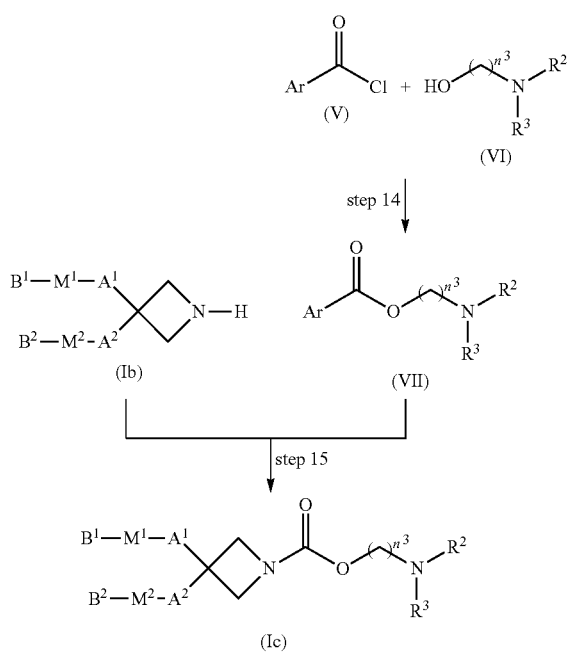

wherein $A^1$, $A^2$, $B^1$, $B^2$, $M^1$, $M^2$, $R^2$, $R^3$ and $n^3$ are each as defined above, Ar represents a substituted phenyl group such as p-nitrophenyl, o-nitrophenyl, or p-chlorophenyl or an unsubstituted phenyl group.

Step 14

Compound (VII) can be produced by reacting compound (V) with compound (VI) at −20° C. to 150° C. for 5 minutes to 72 hours in the presence of, if necessary, preferably 1 to 10 equivalents of an additive and/or, if necessary, preferably 1 to 10 equivalents of a base, without a solvent or in a solvent.

Examples of the solvent include dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, N-methylpyrrolidone, dimethyl sulfoxide, or the like. These solvents can be used singly or as a mixture.

Examples of the additive include 1-hydroxybenzotriazole, 4-dimethylaminopyridine, or the like.

Examples of the base include potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene (DBU), or the like.

Compound (V) can be obtained as a commercially available product.

Compound (VI) can be obtained as a commercially available product or by a method known in the art (e.g., "The Fifth Series of Experimental Chemistry 14, Synthesis of Organic Compound II", 5th edition, p. 1, Maruzen Co., Ltd. (2005)) or a method equivalent thereto.

Step 15

Compound (Ic) can be produced by reacting compound (Ib) with compound (VII) at −20° C. to 150° C. for 5 minutes to 72 hours in the presence of, if necessary, 1 to 10 equivalents of an additive and/or, if necessary, 1 to 10 equivalents of a base, without a solvent or in a solvent.

Compound (Ib) can be produced by using ammonia as compound (IVa) in step 13 of Production method 2.

Examples of the solvent, the additive and the base include those respectively listed in step 14.

Production Method 4

Compound (I) wherein both of $n^1$ and $n^2$ are 1, both of $Z^1$ and $Z^2$ are hydrogen atoms, and $R^3$ is formula (B) (compound (Id)) can be produced by, for example, a method given below.

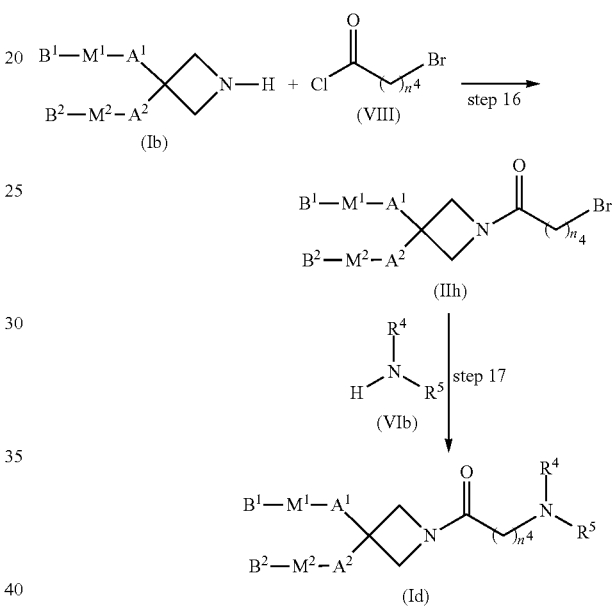

wherein $A^1$, $A^2$, $M^1$, $M^2$, $B^1$, $B^2$, $R^4$, $R^5$ and $n^4$ are each as defined above.

Step 16

Compound (IIh) can be produced by reacting compound (Ib) with compound (VIII) at −20° C. to 150° C. for 5 minutes to 72 hours in the presence of, if necessary, preferably 1 to 10 equivalents of a base, without a solvent or in a solvent.

Examples of the solvent include those listed in step 14.

Examples of the base include those listed in step 6.

Compound (VIII) can be obtained as a commercially available product.

Step 17

Compound (Id) can be produced by reacting compound (IIh) with 1 to 20 equivalents of compound (VIb) at room temperature to 200° C. for 5 minutes to 100 hours, if necessary in the presence of 1 to 10 equivalents of a base, without a solvent or in a solvent.

Examples of the solvent include those listed in steps 2 and 3.

Examples of the base include those listed in step 14.

Compound (VIb) can be obtained as a commercially available product.

Production Method 5

Compound (I) wherein $n^1$ and $n^2$ are, the same or different, an integer from 1 to 4, provided that the case where both of $n^1$ and $n^2$ are 1 is excluded, $R^1$ is a hydrogen atom, C1-C3 alkyl, hydroxyC2-C4 alkyl, or C1-C3 dialkylamino-C2-C4 alkyl, and each of $Z^1$ and $Z^2$ is a hydrogen atom (compound (Ie)) can be produced by, for example, a method given below.

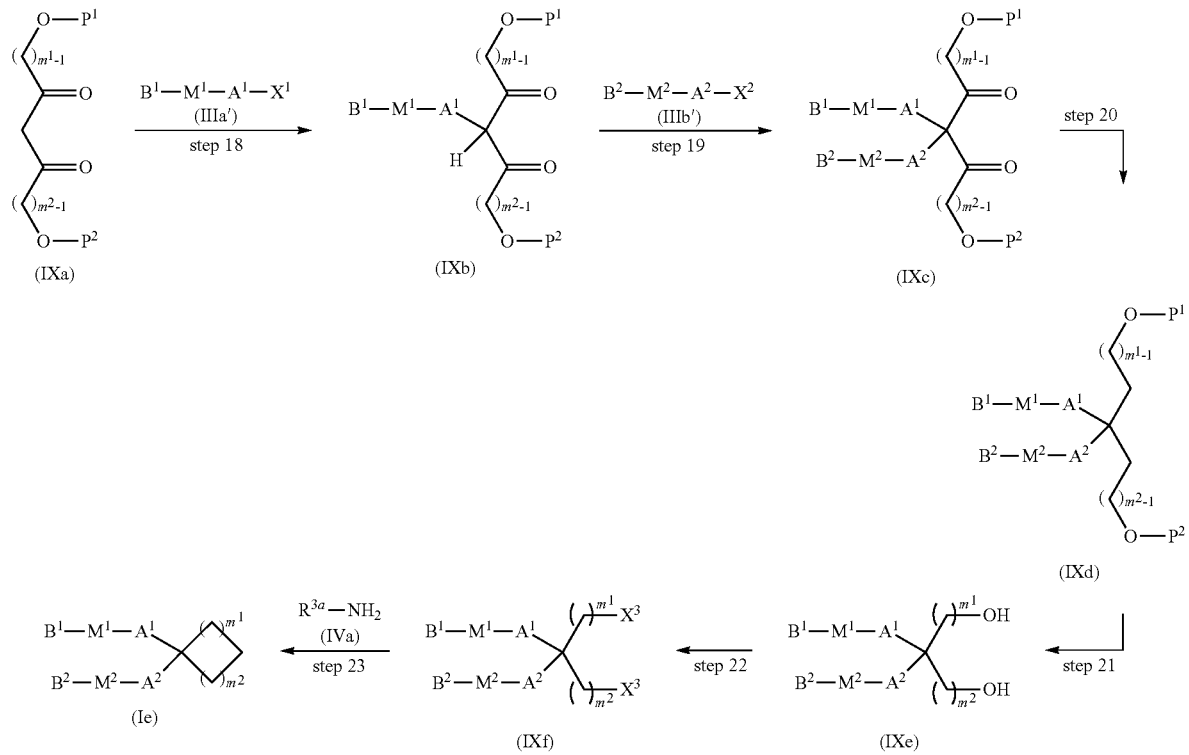

wherein $A^1$, $A^2$, $M^1$, $M^2$, $B^1$, $B^2$, $R^{3a}$, $X^1$, $X^2$ and $X^3$ are each as defined above, $m^1$ and $m^2$ are, the same or different, an integer from 1 to 4, provided that the case where both of $m^1$ and $m^2$ are 1 is excluded, and $P^1$ and $P^2$ are, the same or different, a protective group.

Steps 18 and 19

Compound (IXb) can be produced in the same way as in step 2 by using compound (IXa) instead of di-tert-butyl malonate.

Compound (IXc) can be produced in the same way as in step 3 by using compound (IXb) instead of compound (IIc).

When $B^1$-$M^1$-$A^1$ and $B^2$-$M^2$-$A^2$ are the same, compound (IXc) can be produced by using 2 equivalents or more of compound (IIIa') in step 18.

Protective groups commonly used in organic synthetic chemistry [e.g., protective groups described in Protective Groups in Organic Synthesis, third edition, T. W. Greene, John Wiley & Sons Inc. (1999) or the like] can be used as $P^1$ and $P^2$.

Compound (IXa) is obtained by a known method [e.g., "New Experimental Chemistry 14, Synthesis and Reaction of Organic Compound (II)", first edition, p. 751, Maruzen Co., Ltd. (1977)] or a method equivalent thereto.

Step 20

Compound (IXd) can be produced by reducing compound (IXc) by a known method [e.g., "New Experimental Chemistry 15, Oxidation and Reduction (II)", first edition, Maruzen Co., Ltd. (1977)] or a method equivalent thereto.

Step 21

Compound (IXe) can be produced by respectively removing the protective groups $P^1$ and $P^2$ on compound (IXd) by appropriate methods.

Methods for removing protective groups commonly used in organic synthetic chemistry [e.g., removal methods described in Protective Groups in Organic Synthesis, third edition, T. W. Greene, John Wiley & Sons Inc. (1999) or the like] can be used as the protective group removal methods. The compound of interest can thereby be produced.

Step 22

Compound (IXf) can be produced in the same way as in step 6 by using compound (IXe) instead of compound (IIf).

Step 23

Compound (Ie) can be produced in the same way as in step 7 by using compound (IXf) instead of compound (IIg).

Among compounds (I), compounds other than compounds (Ia) to (Ie) can be produced according to the production methods described above or by the application of general production methods commonly used in organic synthetic chemistry, by adopting starting materials, reagents, or the like, suitable for the structures of the compounds of interest.

The intermediates and the desired compounds in the production methods described above can each be isolated and purified by separation and purification methods commonly used in organic synthetic chemistry, for example, filtration, extraction, washing, drying, concentration, recrystallization, various chromatography techniques, or the like. Each intermediate may be subjected to the next reaction without being particularly purified.

In compound (I) of the present invention, hydrogen ions may be coordinated to a lone pair of electrons on the nitrogen atom in the structure, compound (I) of the present invention may form a salt with a pharmaceutically acceptable anion, and the compound represented by formula (I) of the present invention or the pharmaceutically acceptable salt thereof also encompass such a cationic lipid in which hydrogen ions are coordinated to a lone pair of electrons on the nitrogen atom in the structure.

In the present invention, examples of the pharmaceutically acceptable anion include: inorganic ions such as chloride ions, bromide ions, nitrate ions, sulfate ions, and phosphate ions; and organic acid ions such as acetate ions, oxalate ions, maleate ions, fumarate ions, citrate ions, benzoate ions, and methanesulfonate ions, or the like.

Examples of the pharmaceutically acceptable salt of the compound represented by formula (I) of the present invention include hydrochloride, hydrobromide, nitrate, sulfate, phosphate, acetate, oxalate, maleate, fumarate, citrate, benzoate, methanesulfonate, or the like.

Some compounds (I) of the present invention may have stereoisomers such as geometric isomers and optical isomers, tautomers, or the like. Compound (I) of the present invention encompasses all possible isomers including them, and mixtures thereof.

Some or all of the atoms in compound (I) of the present invention may be replaced with their corresponding isotopic atoms. Compound (I) also encompasses such a compound containing isotopic atoms replaced therefor. For example, some or all of the hydrogen atoms in compound (I) may each be a hydrogen atom having an atomic weight of 2 (deuterium atom).

The compound derived from compound (I) of the present invention by the replacement of some or all of the atoms with their corresponding isotopic atoms can be produced in the same way as in each production method described above by using commercially available building blocks. The compound derived from compound (I) by the replacement of some or all of the hydrogen atoms with deuterium atoms can also be produced by use of, for example, a method which involves deuterating an alcohol, a carboxylic acid, or the like using an iridium complex as a catalyst and heavy water as a deuterium source [see J. Am. Chem. Soc., Vol. 124, No. 10, 2092 (2002)], or the like.

Concrete examples of compound (I) of the present invention are shown in Tables 1 to 3. However, the compound (I) of the present invention is not intended to be limited to them.

TABLE 1

| Compound No. | Structural formula |
|---|---|
| 1 | |
| 2 | |
| 3 | |
| 4 | |

TABLE 2

| Compound No. | Structural formula |
|---|---|
| 5 | |

TABLE 2-continued

| Compound No. | Structural formula |
|---|---|
| 6 | |
| 7 | |
| 8 | |

TABLE 3

| Compound No. | Structural formula |
|---|---|
| 9 | |
| 10 | |
| 11 | |
| 12 | |

The nucleic acid used in the present invention can be any molecule as long as the molecule is obtained by the polymerization of, for example, nucleotides and/or molecules having functions equivalent to nucleotides.

Examples of the nucleic acid include ribonucleic acid (RNA) which is a polymer of ribonucleotides, deoxyribonucleic acid (DNA) which is a polymer of deoxyribonucleotides, chimeric nucleic acids consisting of RNA and DNA, and nucleotide polymers derived from these nucleic acids by the replacement of at least one nucleotide with a molecule having a function equivalent to the nucleotide or the like.

A derivative at least partially containing the structure of the molecule obtained by the polymerization of nucleotides and/or molecules having functions equivalent to nucleotides is also included in the nucleic acid used in the present invention.

In the present invention, uracil U and thymine T can be used interchangeably with each other.

Examples of the molecules having functions equivalent to nucleotides include nucleotide derivatives or the like.

The nucleotide derivative can be any molecule as long as the molecule is, for example, a modified nucleotide. For example, a modified ribonucleotide or deoxyribonucleotide molecule is suitably used for improving nuclease resistance or stabilizing the molecule against the other decomposition factors, for enhancing affinity for a complementary strand nucleic acid, for enhancing cell permeability, or for visualizing the molecule, as compared with RNA or DNA.

Examples of the nucleotide derivative include nucleotides modified at the sugar moiety, nucleotides modified at the phosphodiester bond, nucleotides modified at the base, or the like.

The nucleotide modified at the sugar moiety can be, for example, any nucleotide in which a part or the whole of the chemical structure of its sugar is modified or substituted with an arbitrary substituent or substituted with an arbitrary atom. A 2'-modified nucleotide is preferably used.

Examples of the modifying group in the nucleotide modified at the sugar moiety include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, 2'-SiH$_2$-substituted alkyl, 2'-ONO$_2$, 2'-NO$_2$, 2'-N$_3$, 2'-amino acid residues (which results from the removal of a hydroxy group from the carboxylic acids of amino acids), 2'-O-amino acid residues (as defined in the amino acid residues), or the like.

Examples of the nucleotide modified at the sugar moiety include bridged nucleic acid (BNA) having two cyclic structures by the introduction of a bridged structure to the sugar moiety.

Examples of the bridged nucleic acid include locked nucleic acid (LNA) having the oxygen atom at position 2' and the carbon atom at position 4' bridged via methylene ["Tetrahedron Letters", Volume 38, Issue 50, 1997, Pages 8735-8738, and "Tetrahedron", Volume 54, Issue 14, 1998, Pages 3607-3630], ethylene bridged nucleic acid (ENA) ["Nucleic Acid Research", 32, e175 (2004)], or the like.

Further examples of the nucleotide modified at the sugar moiety also include peptide nucleic acid (PNA) [Acc. Chem. Res., 32, 624 (1999)], oxypeptide nucleic acid (OPNA) [J. Am. Chem. Soc., 123, 4653 (2001)], peptide ribonucleic acid (PRNA) [J. Am. Chem. Soc., 122, 6900 (2000)], or the like.

The modifying group in the nucleotide modified at the sugar moiety is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethylaminooxy)ethyl], 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, or the like, further preferably 2'-O-methyl, 2'-O-ethyl, 2'-fluoro, or the like, most preferably 2'-O-methyl and 2'-O-ethyl.

Further, the modifying group in the nucleotide modified at the sugar moiety can also be defined from its size, preferably the modifying group corresponds to a size from fluoro to —O-butyl, and more preferably the modifying group corresponds to a size from —O-methyl to —O-ethyl.

Examples of the alkyl in the modifying group in the nucleotide modified at the sugar moiety include alkyl having 1 to 6 carbon atoms. The alkyl having 1 to 6 carbon atoms is, for example, methyl, ethyl, propyl, isopropyl, butyl, isobutyl, sec-butyl, tert-butyl, pentyl, isopentyl, neopentyl, hexyl or the like.

Examples of the alkenyl in the modifying group in the nucleotide modified at the sugar moiety include alkenyl having 3 to 6 carbon atoms. Examples thereof include allyl, 1-propenyl, butenyl, pentenyl, hexenyl, or the like.

Examples of the halogen in the modifying group in the nucleotide modified at the sugar moiety include a fluorine atom, a chlorine atom, a bromine atom, an iodine atom, or the like.

Examples of the amino acid in the amino acid residue include aliphatic amino acids (specifically, glycine, alanine, valine, leucine, isoleucine, etc.), hydroxyamino acids (specifically, serine, threonine, etc.), acidic amino acids (specifically, aspartic acid, glutamic acid, etc.), acidic amino acid amides (specifically, asparagine, glutamine, etc.), basic amino acids (specifically, lysine, hydroxylysine, arginine, ornithine, etc.), sulfur-containing amino acids (specifically, cysteine, cystine, methionine, etc.), imino acids (specifically, proline, 4-hydroxyproline etc.), or the like.

Examples of the substituent in the substituted alkyl or the substituted alkenyl in the modifying group in the nucleotide modified at the sugar moiety include halogen (as defined above), hydroxy, sulfanyl, amino, oxo, —O— alkyl (the alkyl moiety of the —O-alkyl is as defined in the above-described alkyl having 1 to 6 carbon atoms), —S-alkyl (the alkyl moiety of the —S-alkyl is as defined in the above-described alkyl having 1 to 6 carbon atoms), —NH-alkyl (the alkyl moiety of the —NH-alkyl is as defined in the above-described alkyl having 1 to 6 carbon atoms), dialkylaminooxy (the two alkyl moieties of the dialkylaminooxy are, the same or different, as defined in the above-described alkyl having 1 to 6 carbon atoms), dialkylamino (the two alkyl moieties of the dialkylamino are, the same or different, as defined in the above-described alkyl having 1 to 6 carbon atoms), dialkylaminoalkyloxy (the two alkyl moieties of the dialkylaminoalkyloxy are, the same or different, as defined in the above-described alkyl having 1 to 6 carbon atoms, and the alkylene moiety means a moiety obtained by removal of one hydrogen atom from the alkyl), or the like. The number of substituents is preferably 1 to 3.

The nucleotide modified at the phosphodiester bond can be any nucleotide in which a part or the whole of the chemical structure of its phosphodiester bond is modified or substituted with an arbitrary substituent or substituted with an arbitrary atom. Examples thereof include a nucleotide resulting from the substitution of the phosphodiester bond with a phosphorothioate bond, a nucleotide resulting from the substitution of the phosphodiester bond with a phosphorodithioate bond, a nucleotide resulting from the substitution of the phosphodiester bond with an alkyl phosphonate bond, a nucleotide resulting from the substitution of the phosphodiester bond with a phosphoramidate bond, or the like.

The nucleotide modified at the base can be any nucleotide in which a part or the whole of the chemical structure of its base is modified or substituted with an arbitrary substituent or substituted with an arbitrary atom.

Examples thereof include a nucleotide resulting from the substitution of an oxygen atom in the base with a sulfur atom, a nucleotide resulting from the substitution of a hydrogen atom with a C1-C6 alkyl group, a nucleotide resulting from the substitution of a methyl group with a hydrogen atom or a C2-C6 alkyl group, a nucleotide resulting from the protection of an amino group with a protective group such as a C1-C6 alkyl group or a C1-C6 alkanoyl group, or the like.

Examples of the nucleotide derivative include nucleotide derivatives that are modified nucleotides or each have at least one modified sugar moiety, phosphodiester bond or base, and contain an additional chemical substance, such as lipid, phospholipid, phenazine, folate, phenanthridine, anthraquinone, acridine, fluorescein, rhodamine, coumarin, or dye, added thereto, and specifically include 5'-polyamine-added nucleotide derivatives, cholesterol-added nucleotide derivatives, steroid-added nucleotide derivatives, bile acid-added nucleotide derivatives, vitamin-added nucleotide derivatives, green fluorescent dye (Cy3)-added nucleotide derivatives, red fluorescent dye (Cy5)-added nucleotide derivatives, fluorescein (6-FAM)-added nucleotide derivatives, biotin-added nucleotide derivatives, or the like.

In the nucleic acid used in the present invention, the nucleotide or the nucleotide derivative may form a bridged structure, such as an alkylene structure, a peptide structure, a nucleotide structure, an ether structure, an ester structure, and a structure combined with at least one of these structures, with another nucleotide or nucleotide derivative within the nucleic acid.

Examples of the nucleic acid used in the present invention preferably include nucleic acids silencing a target gene and more preferably include nucleic acids having a silencing effect on a target gene through the use of RNA interference (RNAi).

The target gene in the present invention is not particularly limited as long as the gene is expressed by producing mRNA, examples thereof include a gene related to tumor or inflammation.

Examples of the a gene related to tumor or inflammation of the target gene include genes encoding proteins such as vascular endothelial growth factor receptor, fibroblast growth factor, fibroblast growth factor receptor, platelet-derived growth factor, platelet-derived growth factor receptor, hepatocyte growth factor, hepatocyte growth factor receptor, Kruppel-like factor, expressed sequence tag (Ets) transcription factor, nuclear factor, hypoxia-inducible factor, cell cycle-related factor, chromosomal replication-related factor, chromosomal repair-related factor, microtubule-related factor, growth signal pathway-related factor, growth-related transcription factor, and apoptosis-related factor, or the like, and specifically include vascular endothelial growth factor gene, vascular endothelial growth factor receptor gene, fibroblast growth factor gene, fibroblast growth factor receptor gene, platelet-derived growth factor gene, platelet-derived growth factor receptor gene, hepatocyte growth factor gene, hepatocyte growth factor receptor gene, Kruppel-like factor gene, expressed sequence tag (Ets) transcription factor gene, nuclear factor gene, hypoxia-inducible factor gene, cell cycle-related factor gene, chromosomal replication-related factor gene, chromosomal repair-related factor gene, microtubule-related factor gene (e.g., CKAP5 gene or the like), growth signal pathway-related factor gene (e.g., KRAS gene or the like), growth-related transcription factor gene, apoptosis-related factor (e.g., BCL-2 gene or the like), or the like.

The target gene according to the present invention is preferably, for example, a gene expressed in the liver, the lung, the kidney, the digestive tract, the central nervous system or the spleen. Examples thereof include genes related to tumor or inflammation, and genes encoding proteins such as hepatitis B virus genome, hepatitis C virus genome, apolipoprotein (APO), hydroxymethylglutaryl (HMG) CoA reductase, kexin type 9 serine protease (PCSK9), factor 12, glucagon receptor, glucocorticoid receptor, leukotriene receptor, thromboxane A2 receptor, histamine H1 receptor, carbonic anhydrase, angiotensin-converting enzyme, renin, p53, tyrosine phosphatase (PTP), sodium-dependent glucose transport carrier, tumor necrosis factor, interleukin, hepcidin, trans siren, antithrombin, protein C, and matriptase enzyme (e.g., TMPRSS6 gene or the like), or the like.

Any nucleic acid such as a double-stranded nucleic acid (e.g., siRNA (short interference RNA) and miRNA (micro RNA)) or a single-stranded nucleic acid (e.g., shRNA (short hairpin RNA), antisense nucleic acid and ribozyme) may be used as the nucleic acid silencing a target gene as long as the nucleic acid comprises a nucleotide sequence complementary to, for example, a partial nucleotide sequence of the mRNA of a gene (target gene) encoding a protein or the like and silences the target gene. A double-stranded nucleic acid is preferred.

The nucleic acid comprising a nucleotide sequence complementary to a partial nucleotide sequence of the mRNA of the target gene is referred to as an antisense strand nucleic acid. A nucleic acid comprising a nucleotide sequence complementary to the nucleotide sequence of the antisense strand nucleic acid is also referred to as a sense strand nucleic acid. The sense strand nucleic acid refers to a nucleic acid capable of forming a duplex formation moiety by pairing with the antisense strand nucleic acid, such as a nucleic acid itself consisting of the partial nucleotide sequence of the target gene.

The double-stranded nucleic acid refers to a nucleic acid having a duplex formation moiety composed of paired two strands. The duplex formation moiety refers to a part in which nucleotides constituting the double-stranded nucleic acid, or derivatives thereof have formed a duplex by constituting base pairs.

The base pairs constituting the duplex formation moiety are usually 15 to 27 base pairs, preferably 15 to 25 base pairs, more preferably 15 to 23 base pairs, further preferably 15 to 21 base pairs, furthermore preferably 15 to 19 base pairs.

For example, a nucleic acid consisting of a partial sequence of the mRNA of the target gene, or a nucleic acid derived from the nucleic acid by the substitution, deletion or addition of 1 to 3 bases, preferably 1 or 2 bases, more preferably 1 base, and having silencing activity against the target protein is suitably used as the antisense strand nucleic acid of the duplex formation moiety. Each single-stranded nucleic acid constituting the double-stranded nucleic acid usually consists of a sequence of 15 to 30 bases (nucleosides), preferably 15 to 29 bases, more preferably 15 to 27 bases, further preferably 15 to 25 bases, furthermore preferably 17 to 23 bases, particularly preferably 19 to 21 bases.

Either of the antisense strand or the sense strand constituting the double-stranded nucleic acid, or both of these nucleic acids may have a non-duplex-forming additional nucleic acid on the 3' or 5' side subsequent to the duplex formation moiety. This non-duplex-forming moiety is also referred to as an overhang.

Examples of the double-stranded nucleic acid include a double-stranded nucleic acid having an overhang consisting of 1 to 4 bases, usually 1 to 3 bases, at the 3' end or the 5' end of at least one of the strands.

A double-stranded nucleic acid having an overhang consisting of 2 bases is preferably used, and a double-stranded nucleic acid having an overhang consisting of dTdT or UU is more preferably used.

The overhang can be located in only the antisense strand, only the sense strand, and both of the antisense strand and the sense strand. A double-stranded nucleic acid having overhangs in both of the antisense strand and the sense strand is preferable.

A sequence partially or completely matching the nucleotide sequence of the mRNA of the target gene, or a sequence partially or completely matching the nucleotide sequence of a complementary strand of the mRNA of the target gene may be used subsequently to the duplex formation moiety.

For example, a nucleic acid molecule that forms the double-stranded nucleic acid by the action of ribonuclease such as Dicer (International Publication No. WO 2005/089287), a double-stranded nucleic acid having no 3'-terminal or 5'-terminal overhang, or the like can also be used as the nucleic acid silencing the target gene.

When the double-stranded nucleic acid is siRNA, preferably, the antisense strand is an antisense strand in which a sequence of at least the 1st to 17th bases (nucleosides) counted from the 5' end toward the 3' end is a sequence of bases complementary to a sequence of 17 consecutive bases of the mRNA of the target gene. More preferably, the antisense strand is an antisense strand in which a sequence of the 1st to 19th bases counted from the 5' end toward the 3' end is a sequence of bases complementary to a sequence of 19 consecutive bases of the mRNA of the target gene, a sequence of the 1st to 21st bases counted from the 5' end toward the 3' end is a sequence of bases complementary to a sequence of 21 consecutive bases of the mRNA of the target gene, or a sequence of the 1st to 25th bases counted from the 5' end toward the 3' end is a sequence of bases complementary to a sequence of 25 consecutive bases of the mRNA of the target gene.

When the nucleic acid used in the present invention is siRNA, preferably 10 to 70%, more preferably 15 to 60%, further preferably 20 to 50%, of sugars in the nucleic acid is ribose substituted at position 2' with a modifying group. The ribose substituted at position 2' with a modifying group according to the present invention means that the hydroxy group at position 2' of the ribose is substituted with a modifying group. The resulting configuration may be the same as or different from that of the hydroxy group at position 2' of the ribose and is preferably the same as that of the hydroxy group at position 2' of the ribose. Examples of the modifying group in the ribose substituted at position 2' therewith include those listed in the definition of the modifying group in the 2'-modified nucleotide in the nucleotide modified at the sugar moiety, and a hydrogen atom. The modifying group is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethyl)aminooxy]ethyl, 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, a hydrogen atom, or the like, further preferably 2'-O-methyl, 2'-O-ethyl, 2'-fluoro, a hydrogen atom, or the like, most preferably 2'-O-methyl and 2'-O-fluoro.

The nucleic acid used in the present invention encompasses derivatives in which, for example, an oxygen atom contained in a phosphoric acid moiety, an ester moiety, or the like in the structure of the nucleic acid, or the like is substituted with a different atom such as a sulfur atom.

The hydroxy group at position 5' of a sugar attached to the 5' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The hydroxy group at position 3' of a sugar attached to the 3' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The single-stranded nucleic acid can be, for example, any nucleic acid consisting of a sequence complementary to a sequence consisting of 15 to 27 consecutive bases (nucleosides), preferably 15 to 25 consecutive bases, more preferably 15 to 23 consecutive bases, further preferably 15 to 21 consecutive bases, particularly preferably 15 to 19 consecutive bases, of the target gene, or any nucleic acid derived from the nucleic acid by the substitution, deletion or addition of 1 to 3 bases, preferably 1 or 2 bases, more preferably 1 base, and having silencing activity against the target protein.

The single-stranded nucleic acid preferably consists of a sequence of 15 to 30 bases (nucleosides), more preferably 15 to 27 bases, further preferably 15 to 25 bases, particularly preferably 15 to 23 bases.

A linkage via a spacer sequence (spacer oligonucleotide) of the antisense strand and the sense strand constituting the double-stranded nucleic acid may be used as the single-stranded nucleic acid. The spacer oligonucleotide is preferably a single-stranded nucleic acid molecule of 6 to 12 bases. Its 5'-terminal sequence is preferably UU. Examples of the spacer oligonucleotide include a nucleic acid consisting of a sequence UUCAAGAGA. The order in which the antisense strand and the sense strand are linked via the spacer oligonucleotide can be any order in which either of the strands may be positioned on the 5' side.

The single-stranded nucleic acid which is linked via a spacer oligonucleotide of the antisense strand and the sense strand constituting the double-stranded nucleic acid is preferably a single-stranded nucleic acid such as shRNA having a duplex formation moiety by, for example, a stem-loop structure. The single-stranded nucleic acid such as shRNA is usually 50 to 70 bases long.

A nucleic acid of 70 bases or smaller in length, preferably 50 bases or smaller in length, more preferably 30 bases or smaller in length, designed to form the single-stranded nucleic acid or the double-stranded nucleic acid by the action of ribonuclease or the like may be used.

The nucleic acid used in the present invention can be produced by use of a known RNA or DNA synthesis method and RNA or DNA modification method.

The composition of the present invention contains the compound represented by formula (I) of the present invention or the pharmaceutically acceptable salt thereof (cationic lipid) and a nucleic acid.

The composition of the present invention can be, for example, a complex of the cationic lipid of the present invention and the nucleic acid.

The composition of the present invention is a composition containing the cationic lipid of the present invention, a neutral lipid and/or a polymer, and a nucleic acid, and can be, for example, a complex of the cationic lipid of the present invention, the neutral lipid and/or the polymer and the nucleic acid.

The composition of the present invention may contain a lipid membrane with which the complex is enclosed.

The lipid membrane may be a lipid monolayer (lipid monomolecular membrane) or a lipid bilayer (lipid bimolecular membrane). The cationic lipid of the present invention, a neutral lipid and/or a polymer may be contained in the lipid membrane.

A cationic lipid other than the cationic lipid which is the compound represented by formula (I) of the present invention or the pharmaceutically acceptable salt thereof may be contained in the complex and/or the lipid membrane.

Other examples of the composition of the present invention also include a composition containing a complex of a cationic lipid other than the cationic lipid of the present invention and the nucleic acid, or a complex of a cationic lipid other than the cationic lipid of the present invention combined with a neutral lipid and/or a polymer and the nucleic acid, and a lipid membrane with which the complex is enclosed, wherein the cationic lipid of the present invention is contained in the lipid membrane, or the like. In this case as well, the lipid membrane may be a lipid monolayer (lipid monomolecular membrane) or a lipid bilayer (lipid bimolecular membrane). A cationic lipid other than the cationic lipid of the present invention, a neutral lipid and/or a polymer may be contained in the lipid membrane.

The composition of the present invention is preferably a composition containing a complex of the cationic lipid of the present invention and the nucleic acid, a composition containing a complex of the cationic lipid of the present invention and the nucleic acid, and a lipid membrane with which the complex is enclosed, wherein the cationic lipid of the present invention is contained in the lipid membrane, and a composition containing a complex of a cationic lipid other than the cationic lipid of the present invention and the nucleic acid, and a lipid membrane with which the complex is enclosed, wherein the cationic lipid of the present invention is contained in the lipid membrane, more preferably a composition containing a complex of the cationic lipid of the present invention and the nucleic acid, and a composition containing a complex of the cationic lipid of the present invention and the nucleic acid, and a lipid membrane with which the complex is enclosed, wherein the cationic lipid of the present invention is contained in the lipid membrane.

In any of the cases, a neutral lipid and/or a polymer may be contained in the lipid membrane. Also, a cationic lipid other than the cationic lipid of the present invention may be contained in the complex and/or the lipid membrane.

Examples of the form of the complex include a complex of the nucleic acid and a membrane (inverse micelle) consisting of a lipid monolayer (monomolecular layer), a complex of the nucleic acid and a liposome, and a complex of the nucleic acid and a micelle, or the like, and preferably include a complex of the nucleic acid and a membrane consisting of a lipid monolayer, and a complex of the nucleic acid and a liposome.

Examples of the composition containing a lipid membrane with which the complex is enclosed include liposomes and lipid nanoparticles in which the complex is enclosed with any number of lipid membranes, or the like.

One or more cationic lipids of the present invention may be used in the composition of the present invention. Also, the cationic lipid of the present invention may be mixed with a cationic lipid other than the cationic lipid of the present invention.

Examples of the cationic lipid other than the cationic lipid of the compound represented by formula (I) or a pharmaceutically acceptable salt thereof of the present invention include: N-[1-(2,3-dioleyloxy)propyl]—N,N,N-trimethylammonium chloride (DOTMA), N-(2,3-di-(9-(Z)-octadecenoyloxy))-prop-1-yl-N,N,N-trimethylammonium chloride (DOTAP), or the like, disclosed in Japanese Patent Laid-Open No. 61-161246 (U.S. Pat. No. 5,049,386); N-[1-(2,3-dioleyloxypropyl)]-N,N-dimethyl-N-hydroxyethyl ammonium bromide (DORIE), 2,3-dioleyloxy-N-[2-(sperminecarboxamide)ethyl]-N,N-dimethyl-1-propanaminium trifluoroacetic acid (DOSPA), or the like, disclosed in International Publication Nos. WO 91/16024 and WO 97/019675; DLinDMA or the like, disclosed in International Publication No. WO 2005/121348; DLin-K-DMA disclosed in International Publication No. WO 2009/086558; and (3R,4R)-3,4-bis((Z)-hexadec-9-enyloxy)-1-methylpyrrolidine, N-methyl-N,N-bis(2-((Z)-octadec-6-enyloxy)ethyl)amine, or the like, disclosed in International Publication No. WO 2011/136368.

Examples of the cationic lipid other than the cationic lipid of the present invention preferably include cationic lipids having a tertiary amine site having two unsubstituted alkyl groups or a quaternary ammonium site having three unsubstituted alkyl groups, such as DOTMA, DOTAP, DORIE, DOSPA, 1,2-dilinoleyloxy-N,N-dimethylaminopropane (DLinDMA), and 2,2-dilinoleyl-4-dimethylaminomethyl-[1,3]-dioxolane (DLin-K-DMA), and more preferably include cationic lipids having the tertiary amine site.

The unsubstituted alkyl groups in the tertiary amine site or the quaternary ammonium site are more preferably methyl groups.

The composition of the present invention may also contain a compound chemically analogous to the nucleic acid in addition to the nucleic acid.

The composition of the present invention can be produced according to a production method known in the art or a method equivalent thereto and may be produced by any production method. For example, a liposome preparation method known in the art can be applied to the production of a composition containing a liposome, which is a composition.

Examples of the liposome preparation method known in the art include a liposome preparation method of Bangham et al. [see "J. Mol. Biol.", 1965, Vol. 13, p. 238-252], an ethanol injection method [see "J. Cell Biol.", 1975, Vol. 66, p. 621-634], a French press method [see "FEBS Lett.", 1979, Vol. 99, p. 210-214], a freezing-thawing method [see "Arch. Biochem. Biophys.", 1981, Vol. 212, p. 186-194], a reverse-phase evaporation method [see "Proc. Natl. Acad. Sci. USA", 1978, Vol. 75, p. 4194-4198], a pH gradient method (see e.g., Japanese Patent Nos. 2572554 and 2659136 or the like), or the like.

Examples of the solution for dispersing the liposome in the production of the liposome include water, an acid, an alkali, various buffer solutions, physiological saline, an amino acid transfusion, or the like.

In the production of the liposome, for example, an antioxidant such as citric acid, ascorbic acid, cysteine, and ethylenediaminetetraacetic acid (EDTA); a tonicity agent such as glycerin, glucose, and sodium chloride, or the like may also be added.

The liposome can also be formed, for example, by dissolving the cationic lipid of the present invention, a mixture of the cationic lipid of the present invention and a cationic lipid other than the cationic lipid of the present invention, or the like, for example, in an organic solvent such as ethanol, distilling off the solvent, then adding physiological saline or the like to the residue, and shaking and stirring the mixture to form the liposome.

The composition of the present invention can be produced by, for example, a production method which involves dissolving the cationic lipid of the present invention, or a mixture of the cationic lipid of the present invention and a cationic lipid other than the cationic lipid of the present invention in chloroform in advance, subsequently adding an aqueous solution of the nucleic acid and methanol to the solution, mixing the mixture to form a cationic lipid/nucleic acid complex, further isolating the chloroform layer, and adding polyethylene glycolated phospholipid, a neutral lipid and water to the isolated chloroform layer resulting to form a water-in-oil (W/O) emulsion, which is then treated by the reverse-phase evaporation method (see National Publication of International Patent Application No. 2002-508765), or a production method which involves dissolving the nucleic acid in an aqueous solution of an acidic electrolyte, adding, for example, a mixture of the cationic lipid of the present invention, or a mixture of the cationic lipid of the present invention and a cationic lipid other than the cationic lipid of the present invention (in ethanol) to the solution, decreasing the ethanol concentration to 20 v/v % to prepare a liposome containing the nucleic acid, removing excessive ethanol by dialysis after sizing and filtration, and then dialyzing the sample by further elevating pH to remove the nucleic acid attached to the surface of the composition (see National Publication of International Patent Application No. 2002-501511 and Biochimica et Biophysica Acta, 2001, Vol. 1510, p. 152-166), or the like.

Among the compositions of the present invention, a composition containing a complex of the cationic lipid of the present invention and the nucleic acid, or a lipid nanoparticles containing a complex of a neutral lipid and/or a polymer and the nucleic acid, and a lipid bilayer with which the complex is enclosed with the cationic lipid of the present invention can be produced according to production methods described in, for example, International Publication Nos. WO 02/28367 and WO 2006/080118 or the like.

In the case of producing the composition of the present invention according to production methods described in International Publication Nos. WO 02/28367 and WO 2006/080118 or the like, the composition of the present invention can be produced by producing a complex using components appropriately selected from the cationic lipid of the present invention, a nucleic acid, a neutral lipid and/or a polymer, and a cationic lipid other than the cationic lipid of the present invention, dispersing the complex in water or a 0 to 40% aqueous ethanol solution without dissolution (liquid A), aside from this, dissolving lipid membrane components to enclose the complex in, for example, an aqueous ethanol solution (liquid B), mixing the liquid A and the liquid B at a volume ratio of 1:1 to 10:1, and further appropriately adding water thereto.

One or more cationic lipids of the present invention or cationic lipids other than the cationic lipid of the present invention can be used as cationic lipids in the liquids A and B. Alternatively, the cationic lipid of the present invention and the cationic lipid other than the cationic lipid of the present invention may be combined and used as a mixture.

In the present invention, during and after production of the composition containing a complex of the cationic lipid of the present invention and the nucleic acid, or a complex of the cationic lipid of the present invention, a neutral lipid and/or a polymer and the nucleic acid, and a lipid membrane with which the complex is enclosed, the composition containing a complex of a cationic lipid other than the cationic lipid of the present invention and the nucleic acid, or a complex of a cationic lipid other than the cationic lipid of the present invention, a neutral lipid and/or a polymer and the nucleic acid, and a lipid membrane with which the complex is enclosed, wherein the cationic lipid of the present invention is contained in the lipid membrane, or the like, the structures of the complex and the membrane may be varied due to the electrostatic interaction between the nucleic acid in the complex and the cationic lipid in the lipid membrane, or the fusion of the cationic lipid in the complex with the cationic lipid in the lipid membrane. Such a composition is also included in the composition of the present invention.

The composition containing the composition of the present invention and the nucleic acid can also be produced according to production methods described in International Publication Nos. WO 02/28367 and WO 2006/080118, or the like, by producing a complex of the nucleic acid, preferably the double-stranded nucleic acid, and a liposome containing the cationic lipid of the present invention and/or a cationic lipid other than the cationic lipid of the present invention, dispersing the complex in water or a 0 to 40% aqueous ethanol solution without dissolution (liquid A), aside from this, dissolving the cationic lipid of the present invention and/or a cationic lipid other than the cationic lipid of the present invention in an aqueous ethanol solution (liquid B), mixing the liquid A and the liquid B at a volume ratio of 1:1 to 10:1, and further appropriately adding water thereto.

The composition obtained by this method is preferably a composition containing a complex of the cationic lipid and the nucleic acid, and a lipid membrane with which the complex is enclosed, or a composition containing a complex of the nucleic acid and a membrane (inverse micelle) consisting of a lipid monolayer containing the cationic lipid, and a lipid membrane with which the complex is enclosed. The lipid membrane in the composition may be any of a lipid monolayer (lipid monomolecular membrane), a lipid bilayer (lipid bimolecular membrane), and a multilamellar membrane.

It is preferable to adjust the size of liposome in the complex of the nucleic acid and the liposome in advance to preferably 10 nm to 400 nm, more preferably 20 nm to 110 nm, further preferably 30 nm to 80 nm as an average particle size. A neutral lipid and/or a polymer may be contained in the complex and/or the lipid membrane. The liquid A may have an ethanol concentration of 20 to 70% as long as the complex of the liposome and the nucleic acid can be formed.

Instead of mixing the liquid A and the liquid B in equal amounts, the liquid A and the liquid B may be mixed at a ratio that does not dissolve the complex after the mixing and adjusts an ethanol concentration so as not to dissolve the cationic lipid in the liquid B. Preferably, the liquid A and the liquid B may instead be mixed at a ratio that neither dissolves the complex nor the cationic lipid in the liquid B and creates an aqueous ethanol solution having an ethanol concentration of 30 to 60%. Alternatively, the liquid A and the liquid B may be mixed at a ratio that adjusts an ethanol concentration so as not to dissolve the complex after the mixing of the liquid A and the liquid B, and the ethanol concentration is further adjusted by the addition of water so as not to dissolve the cationic lipid in the liquid B.

The composition obtained by this production method is preferably a composition containing a complex of the cationic lipid and the nucleic acid, and a lipid membrane with which the complex is enclosed, or a composition containing a complex of a membrane (inverse micelle) consisting of a lipid monolayer containing the cationic lipid and the nucleic acid, and a lipid membrane with which the complex is enclosed, wherein the cationic lipid is contained in the lipid membrane. This production method is excellent in productivity (yield and/or homogeneity) of this production method.

In the composition of the present invention, the total number of molecules of the cationic lipid of the present invention in the complex is preferably 0.5 to 4 times, more preferably 1.5 to 3.5 times, further preferably 2 to 3 times the number of phosphorus atoms of the nucleic acid.

The total number of molecules of the cationic lipid of the present invention and the cationic lipid other than the cationic lipid of the present invention in the complex is preferably 0.5 to 4 times, more preferably 1.5 to 3.5 times, further preferably 2 to 3 times the number of phosphorus atoms of the nucleic acid.

In the composition of the present invention, the total number of molecules of the cationic lipid of the present invention in the composition containing the complex and a lipid membrane with which the complex is enclosed is preferably 1 to 10 times, more preferably 2.5 to 9 times, further preferably 3.5 to 8 times the number of phosphorus atoms of the nucleic acid.

The total number of molecules of the cationic lipid of the present invention and the cationic lipid other than the cationic lipid of the present invention in this composition is preferably 1 to 10 times, more preferably 2.5 to 9 times, further preferably 3.5 to 8 times the number of phosphorus atoms of the nucleic acid.

The neutral lipid can be any of simple lipids, complex lipids, and derived lipids. Examples thereof include phospholipids, glyceroglycolipids, sphingoglycolipids, sphingoid, sterol, or the like.

When the composition of the present invention contains a neutral lipid, the total number of molecules of the neutral lipid is preferably 0.1 to 2 times, more preferably 0.2 to 1.5 times, further preferably 0.3 to 1.2 times the total number of molecules of the cationic lipid of the present invention and the cationic lipid other than the cationic lipid of the present invention.

In any composition of the present invention, the neutral lipid may be contained in the complex or may be contained in the lipid membrane with which the complex is enclosed. More preferably, the neutral lipid is contained at least in the lipid membrane with which the complex is enclosed. Further preferably, the neutral lipid is contained in both of the complex and the lipid membrane with which the complex is enclosed.

Examples of the phospholipid as the neutral lipid include natural or synthetic phospholipids such as phosphatidylcholines (specifically, soybean phosphatidylcholine, egg phosphatidylcholine (EPC), distearoyl phosphatidylcholine (DSPC), dipalmitoyl phosphatidylcholine (DPPC), palmitoyl oleoyl phosphatidylcholine (POPC), dimyristoyl phosphatidylcholine (DMPC), dioleoyl phosphatidylcholine (DOPC), etc.), phosphatidylethanolamines (specifically distearoyl phosphatidylethanolamine (DSPE), dipalmitoyl phosphatidylethanolamine (DPPE), dioleoyl phosphatidylethanolamine (DOPE), dimyristoyl phosphatidylethanolamine (DMPE), 16-O-monomethyl PE, 16-0-dimethyl PE, 18-1-trans PE, palmitoyl oleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyl oleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphoric acid, etc.), glycerophosphonolipids, sphingophosphonolipids, natural lecithins (specifically, egg lecithin, soybean lecithin, etc.), hydrogenated phospholipids (specifically, hydrogenated soybean phosphatidylcholine, etc.), or the like.

Examples of the glyceroglycolipid as the neutral lipid include sulfoxyribosyl glyceride, diglycosyl diglyceride, digalactosyl diglyceride, galactosyl diglyceride, glycosyl diglyceride, or the like.

Examples of the sphingoglycolipid as the neutral lipid include galactosyl cerebroside, lactosyl cerebroside, ganglioside, or the like.

Examples of the sphingoid as the neutral lipid include sphingan, icosasphingan, sphingosine, and derivatives of the foregoing, or the like.

Examples of the derivatives include substances derived from sphingan, icosasphingan, sphingosine, or the like by the conversion of —NH$_2$ to —NHCO(CH$_2$)$_x$CH$_3$ wherein x is an integer from 0 to 18 and is particularly preferably 6, 12, or 18).

Examples of the sterol as the neutral lipid include cholesterol, dihydrocholesterol, lanosterol, β-sitosterol, campesterol, stigmasterol, brassicasterol, erugosterol, fucosterol, 3β-[N—(N',N'-dimethylaminoethyl)carbamoyl]cholesterol (DC-Chol), or the like.

Examples of the polymer include polymers such as proteins, albumin, dextran, Polyfect, chitosan, dextran sulfate, poly-L-lysine, polyethylenimine, polyaspartic acid, styrene-maleic acid copolymers, isopropylacrylamide-acrylpyrrolidone copolymers, polyethylene glycol-modified dendrimers, polylactic acid, polylactic acid-polyglycolic acid, polyethylene glycolated polylactic acid, or the like.

The polymer may be a micelle consisting of one or more of salts of any of the polymers listed above.

Examples of the salt of the polymer include metal salts, ammonium salts, acid-addition salts, organic amine-addition salts, amino acid-addition salts, or the like.

Examples of the metal salts include: alkali metal salts such as lithium salt, sodium salt, and potassium salt; alkaline earth metal salts such as magnesium salt and calcium salt; aluminum salts; and zinc salts, or the like.

Examples of the ammonium salts include salts of ammonium, tetramethylammonium, or the like.

Examples of the acid-addition salts include: inorganic acid salts such as hydrochloride, sulfate, nitrate, and phosphate; and organic acid salts such as acetate, maleate, fumarate, and citrate.

Examples of the organic amine-addition salts include addition salts of morpholine, piperidine, or the like.

Examples of the amino acid-addition salts include addition salts of glycine, phenylalanine, aspartic acid, glutamic acid, lysine, or the like.

The composition of the present invention preferably contains a lipid derivative or a fatty acid derivative of one or more substances selected from, for example, sugars, peptides, nucleic acids and water-soluble polymers, a surfactant, or the like. The derivative, the surfactant or the like may be contained in the complex or may be contained in the lipid membrane with which the complex is enclosed, and is more preferably contained in both of the complex and the lipid membrane with which the complex is enclosed.

When the composition of the present invention contains a lipid derivative or a fatty acid derivative of one or more substances selected from sugars, peptides, nucleic acids, and water-soluble polymers, the total number of molecules of the lipid derivative or the fatty acid derivative of one or more substances selected from sugars, peptides, nucleic acids, and water-soluble polymers is preferably 0.01 to 0.3 times, more preferably 0.02 to 0.25 times, further preferably 0.03 to 0.15 times the total number of molecules of the cationic lipid of the present invention and the cationic lipid other than the cationic lipid of the present invention.

Examples of the lipid derivative or the fatty acid derivative of one or more substances selected from sugars, peptides, nucleic acids, and water-soluble polymers, or the surfactant preferably include glycolipids, and lipid derivatives or fatty acid derivatives of water-soluble polymers and more preferably include lipid derivatives or fatty acid derivatives of water-soluble polymers.

The lipid derivative or the fatty acid derivative of one or more substances selected from sugars, peptides, nucleic acids, and water-soluble polymers, or the surfactant is preferably a two-faced substance in which a part of the molecule has the properties of binding to other constituents of the composition of the present invention via, for example, hydrophobic affinity, electrostatic interaction, or the like and the other moiety has the properties of binding to a solvent for use in the production of the composition via, for example, hydrophilic affinity, electrostatic interaction, or the like.

Examples of the lipid derivatives or the fatty acid derivatives of sugars, peptides or nucleic acids include substances obtained by the binding of sugars such as sucrose, sorbitol, and lactose, peptides such as casein-derived peptides, ovalbumin-derived peptides, soybean-derived peptides, and glutathione, or nucleic acids such as DNA, RNA, plasmids, siRNA, and oligo-deoxy nucleotides (ODN) to the neutral lipids or the cationic lipids of the present invention listed in the definition of the composition or to fatty acids such as stearic acid, palmitic acid, myristic acid, and lauric acid, or the like.

Examples of the lipid derivatives or the fatty acid derivatives of sugars also include the glyceroglycolipids or the sphingoglycolipids, or the like.

Examples of the lipid derivatives or the fatty acid derivatives of water-soluble polymers include substances obtained by the binding of polyethylene glycol, polyglycerin, polyethylenimine, polyvinyl alcohol, polyacrylic acid, polyacrylamide, oligosaccharide, dextrin, water-soluble cellulose, dextran, chondroitin sulfate, polyglycerin, chitosan, polyvinylpyrrolidone, polyaspartic acid amide, poly-L-lysine, mannan, pullulan, or oligoglycerol, or the like or derivatives of the foregoing to the neutral lipids or the cationic lipids of the present invention or to fatty acids such as stearic acid, palmitic acid, myristic acid, and lauric acid. Examples thereof more preferably include lipid derivatives or fatty acid derivatives of polyethylene glycol or polyglycerin, and further preferably include lipid derivatives or fatty acid derivatives of polyethylene glycol.

The lipid derivatives or the fatty acid derivatives of water-soluble polymers may be salts of thereof.

Examples of the lipid derivatives or the fatty acid derivatives of polyethylene glycol include polyethylene glycolated lipids [specifically, polyethylene glycol-phosphatidylethanolamine (more specifically, 1,2-distearoyl-sn-glycero-3-phosphoethanolamine-N-[methoxy(polyethylene glycol)-2000] (PEG-DSPE), and 1,2-dimyristoyl-sn-glycero-3-phosphoethanolamine-N-[methoxy(polyethylene glycol)-2000] (PEG-DMPE), etc.), polyoxyethylene hydrogenated castor oil 60, CREMOPHOR EL, etc.], polyethylene glycol sorbitan fatty acid esters (specifically, polyoxyethylene sorbitan monooleate, etc.), or the like, and polyethylene glycol fatty acid esters and more preferably include polyethylene glycolated lipids.

Examples of the lipid derivatives or the fatty acid derivatives of polyglycerin include polyglycerinated lipids (specifically, polyglycerin-phosphatidylethanolamine, etc.), polyglycerin fatty acid esters, or the like and preferably include polyglycerinated lipids.

Examples of the surfactant include polyoxyethylene sorbitan monooleate (specifically, polysorbate 80, etc.), polyoxyethylene polyoxypropylene glycol (specifically, Pluronic (registered trademark) F68, etc.), sorbitan fatty acid esters (specifically, sorbitan monolaurate, sorbitan monooleate, etc.), polyoxyethylene derivatives (specifically, polyoxyethylene hydrogenated castor oil 60, polyoxyethylene lauryl alcohol, etc.), glycerin fatty acid esters, polyethylene glycol alkyl ethers, or the like and preferably include polyoxyethylene polyoxypropylene glycol, glycerin fatty acid esters and polyethylene glycol alkyl ethers.

The complex and the lipid membrane in the composition of the present invention can each be arbitrarily surface-modified with, for example, a water-soluble polymer or the like[see D. D. Lasic and F. Martin ed., "Stealth Liposomes" (USA), CRC Press Inc.), 1995, p. 93-102].

Examples of the water-soluble polymer that may be used in the surface modification include polyethylene glycol, polyglycerin, polyethylenimine, polyvinyl alcohol, polyacrylic acid, polyacrylamide, oligosaccharides, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or the like and preferably include dextran, pullulan, mannan, amylopectin, hydroxyethyl starch, or the like.

The lipid derivative, the fatty acid derivative of one or more substances selected from sugars, peptides, nucleic acids, and water-soluble polymers (as defined above), or the like can also be used in the surface modification. The surface modification is a method for allowing the complex and the lipid membrane in the composition of the present invention to contain the lipid derivative or the fatty acid derivative of one or more substances selected from sugars, peptides, nucleic acids, and water-soluble polymers, or the surfactant.

A targeting ligand can be bonded directly to the surface of the composition of the present invention through a covalent bond to a polar head residue of a lipid component in the composition of the present invention (see International Publication No. WO 2006/116107).

The average particle size of the complex or the lipid membrane with which the complex is enclosed in the composition of the present invention can be arbitrarily selected, if desired.

Examples of a method for adjusting the average particle size include an extrusion method and a method of mechanically pulverizing a large multilamellar vesicle (MLV) or the like (specifically, using Manton Gaulin, Microfluidizer, etc.) [see R. H. Muller, S. Benita and B. Bohm ed., "Emulsion and Nanosuspensions for the Formulation of Poorly Soluble Drugs", Germany, Scientific Publishers Stuttgart, 1998, p. 267-294], or the like.

The size of the complex in the composition of the present invention is preferably approximately 5 nm to 200 nm, more preferably approximately 20 nm to 150 nm, further preferably approximately 20 nm to 80 nm, in terms of an average particle size.

The size of the composition of the present invention (the lipid membrane with which the complex is enclosed) is preferably approximately 10 nm to 300 nm, more preferably approximately 30 nm to 200 nm, further preferably approximately 50 nm to 150 nm, in terms of an average particle size.

The average particle size of the complex or the lipid membrane with which the complex is enclosed in the composition of the present invention can be measured by, for example, a dynamic light scattering method.

The nucleic acid in the composition of the present invention can be introduced into a cell by introducing the composition of the present invention into a mammalian cell.

The in vivo introduction of the composition of the present invention into a mammalian cell can be performed according to procedures of transfection known in the art that can be performed in vivo. For example, the composition of the present invention can be intravenously administered to a mammal including a human and thereby delivered to, for example, an organ or a site having tumor or inflammation so that the nucleic acid in the composition of the present invention is introduced into a cell of the organ or the site that has received the composition. Examples of the organ or the site having tumor or inflammation include, but are not particularly limited to, the digestive tract such as the stomach and the large intestine, the liver, the lung, the spleen, the pancreas, the kidney, the bladder, the skin, vascular vessels, eye balls, or the like. Also, the composition of the present invention can be intravenously administered to a mammal including a human and thereby delivered to, for example, the liver, the lung, the spleen, the digestive tract, the central nervous system and/or the kidney so that the nucleic acid in the composition of the present invention is introduced into a cell of the organ or the site that has received the composition. The cell of the liver, the lung, the spleen, and/or the kidney can be any of normal cells, cells related to tumor or inflammation, and cells related to the other diseases.

Provided that the nucleic acid in the composition of the present invention is a nucleic acid having a silencing effect on a target gene through the use of RNA interference (RNAi), for example, the nucleic acid silencing a target gene or the like can be introduced into a mammalian cell in vivo. As a result, the expression of the target gene can be suppressed.

The recipient is preferably a human.

Provided that the target gene in the present invention is, for example, a gene expressed in the liver, the lung, the kidney, the digestive tract, the central nervous system or the spleen, the composition of the present invention can be used as a therapeutic agent or a prophylactic agent for a disease related to the liver, the lung, the kidney, the digestive tract, the central nervous system or the spleen.

Specifically, the present invention also provides a method for treating a disease related to the liver, the lung, the kidney, the digestive tract, the central nervous system or the spleen, comprising administering the composition of the present invention to a mammal. The recipient is preferably a human, more preferably a human having the disease related to the liver, the lung, the kidney, the digestive tract, the central nervous system or the spleen.

The composition of the present invention can also be used as a tool for verifying the effectiveness of suppression of a target gene in an in vivo drug efficacy evaluation model as to a therapeutic agent or a prophylactic agent for a disease related to the liver, the lung, the kidney, the digestive tract, the central nervous system or the spleen.

The composition of the present invention can also be used as a preparation aimed at, for example, stabilizing the nucleic acid in a biogenic substance such as a blood component (e.g., in blood, the digestive tract, of the like), reducing adverse reactions, enhancing drug accumulation to a tissue or an organ containing an expression site of the target gene, or the like.

When the composition of the present invention is pharmaceutically used as a therapeutic agent or a prophylactic agent for, for example, a disease related to the liver, the lung, the kidney, the digestive tract, the central nervous system or the spleen, or the like, an administration route most effective for treatment is desirably used. Examples of such an administration route can include parenteral or oral administration such as administration into the oral cavity, intratracheal administration, intrarectal administration, subcutaneous administration, intramuscular administration, intravenous administration, or the like. Examples thereof can preferably include intravenous administration and intramuscular administration and more preferably include intravenous administration.

The dose of the composition of the present invention differs depending on the pathological condition or age of the recipient, the administration route, or the like. For example, the composition of the present invention can be administered, for example, at a daily dose of approximately 0.1 µg to 1000 mg in terms of the amount of the nucleic acid.

Examples of the preparation suitable for intravenous administration or intramuscular administration include injections, and a dispersion of the composition of the present invention prepared may be used directly in the form of, for example, an injection or the like.

The suitable preparation is preferably a preparation which is removed the solvents from the dispersion by, for example, filtration, centrifugation, or the like, and a preparation obtained by being supplemented the dispersion with, for example, an excipient such as mannitol, lactose, trehalose, maltose, glycine, or the like and then freeze-dried.

In the case of an injection, the dispersion of the composition of the present invention or the solvent-free or freeze-dried composition is preferably mixed with, for example, water, an acid, an alkali, various buffer solutions, physiological saline, an amino acid transfusion, or the like to prepare the injection. The injection may be prepared by the addition of, for example, an antioxidant such as citric acid, ascorbic acid, cysteine, and EDTA or a tonicity agent such as glycerin, glucose or sodium chloride. Also, the injection can also be cryopreserved by the addition of a cryopreserving agent such as glycerin.

Next, the present invention will be specifically described with reference to Examples, Reference Examples, and Test Examples. However, the present invention is not intended to be limited by these Examples, Reference Examples, and Test Examples.

Proton nuclear magnetic resonance spectra ($^1$H NMR) shown in Examples and Reference Examples were measured at 400 MHz, and no exchangeable proton may be clearly observed depending on compounds and measurement conditions. The multiplicity of signals is indicated as usually used.

Reference Example 1

Dinonyl 11,11-bis(hydroxymethyl)henicosanedioate (Compound IIf-1)

Step 1

Nonan-1-ol (manufactured by Tokyo Chemical Industry Co., Ltd., 6.03 g, 41.8 mmol) was dissolved in dichloromethane (30 mL). To the solution, 10-bromodecanoic acid (manufactured by Tokyo Chemical Industry Co., Ltd., 7.00 g, 27.9 mmol), 1-ethyl-3-(3-dimethylaminopropyl)carbodiimide hydrochloride (manufactured by Tokyo Chemical Industry Co., Ltd., 8.01 g, 41.8 mmol), and dimethylaminopyridine (3.40 g, 27.9 mmol) were added in this order, and the mixture was reacted overnight at room temperature. The reaction mixture was concentrated under reduced pressure, and the obtained residue was purified by silica gel column chromatography (hexane/ethyl acetate=98/2) to obtain nonyl 10-bromodecanoate (5.75 g, yield: 55%).

$^1$H-NMR (CDCl$_3$) δ: 0.88 (t, J=6.8 Hz, 3H), 1.23-1.37 (m, 20H), 1.37-1.45 (m, 2H), 1.57-1.66 (m, 4H), 1.80-1.89 (m, 2H), 2.29 (t, J=7.6 Hz, 2H), 3.40 (t, J=6.8 Hz, 2H), 4.06 (t, J=6.8 Hz, 2H).

Step 2

Di-tert-butyl malonate (manufactured by Tokyo Chemical Industry Co., Ltd., 1.03 mL, 4.62 mmol) was dissolved in tetrahydrofuran (15 mL). To the solution, sodium hydride (manufactured by Nacalai Tesque, Inc., 60% oil, 0.555 g, 11.4 mmol) was added at 0° C., and the mixture was stirred for a while until foaming was no longer observed. A solution of nonyl 10-bromodecanoate (5.24 g, 13.9 mmol) obtained in step 1 in tetrahydrofuran (5 mL) was added thereto at 0° C., and the mixture was then stirred at 70° C. for 2 hours. A saturated aqueous solution of ammonium chloride was added to the reaction mixture, followed by extraction with ethyl acetate. The organic layer was washed with saturated saline, dried over anhydrous magnesium sulfate, then filtered and concentrated under reduced pressure to obtain a crude product of 10,10-di-tert-butyl 1,19-dinonyl nonadecane-1,10,10,19-tetracarboxylate.

The obtained crude product was dissolved in dichloromethane (20 mL). To the solution, trifluoroacetic acid (10 mL, 130 mmol) was added at 0° C., and the mixture was stirred at room temperature for 2 hours. The reaction mixture was concentrated under reduced pressure, and the obtained residue was purified by silica gel column chromatography (chloroform/methanol=99/1 to 90/10) to obtain 2,2-bis(10-(nonyloxy)-10-oxodecyl)malonic acid (1.89 g, yield: 37%).

ESI-MS m/z: 695 (M−H)$^-$

Step 3

2,2-Bis(10-(nonyloxy)-10-oxodecyl)malonic acid (1.84 g, 2.64 mmol) obtained in Step 2 was dissolved in tetrahydrofuran (10 mL). To the solution, a borane-tetrahydrofuran complex (manufactured by Sigma-Aldrich Corp., 1 mol/L, 7.92 mL, 7.92 mmol) was added at 0° C., and the mixture was stirred overnight at room temperature. Water was added to the reaction mixture, followed by extraction with ethyl acetate. The organic layer was washed with saturated saline, dried over anhydrous magnesium sulfate and filtered. The filtrate was concentrated under reduced pressure, and the obtained residue was purified by silica gel column chromatography (hexane/ethyl acetate=90/10 to 40/60) to obtain compound IIf-1 (0.400 g, yield: 23%).

ESI-MS m/z: 670 (M+H)$^+$

Example 1

Dinonyl 10,10'-(1-methylazetidine-3,3-diyl)bis(decanoate) (Compound 1)

Step 1

Compound IIf-1 (0.400 g, 0.598 mmol) obtained in Reference Example 1 was dissolved in dichloromethane (4 mL). To the solution, pyridine (0.484 mL, 5.98 mmol) was added. Trifluoromethanesulfonic anhydride (manufactured by Nacalai Tesque, Inc., 0.303 mL, 1.79 mmol) was added thereto at 0° C., and the mixture was stirred for 30 minutes. Water was added to the reaction mixture, followed by extraction with ethyl acetate. The organic layer was washed with saturated saline, dried over anhydrous magnesium sulfate and filtered. The filtrate was concentrated under reduced pressure to obtain a crude product of dinonyl 11,11-bis(((((trifluoromethyl)sulfonyl)oxy)methyl)henicosanedioate (0.558 g).

The obtained crude product (0.558 g) was dissolved in N,N-dimethylacetamide (4 mL). To the solution, methylamine (manufactured by Tokyo Chemical Industry Co., Ltd., approximately 9.8 mol/L solution in methanol, 0.35 mL, 2.99 mmol) was added, and the mixture was stirred at 60° C. for 1 hour. After cooling to room temperature, water was added to the reaction mixture, followed by extraction with ethyl acetate. The organic layer was washed with saturated saline, dried over anhydrous magnesium sulfate and filtered. The filtrate was concentrated under reduced pressure, and the obtained residue was purified by silica gel column chromatography (NH silica gel, hexane/ethyl acetate=99/1 to 70/30) to obtain compound 1 (0.220 g, yield: 55%).

ESI-MS m/z: 664 (M+H)$^+$; $^1$H-NMR (CDCl$_3$) δ: 0.88 (t, J=6.8 Hz, 6H), 1.09-1.20 (m, 4H), 1.20-1.38 (m, 44H), 1.46-1.54 (m, 4H), 1.56-1.72 (m, 8H), 2.29 (t, J=7.7 Hz, 4H), 2.31 (s, 3H), 2.93 (s, 4H), 4.06 (t, J=6.7 Hz, 4H).

Example 2

Di((Z)-non-2-en-1-yl) 10,10'-(1-methylazetidine-3,3-diyl)bis(decanoate) (Compound 2)

Step 1

Compound 1 (0.170 g, 0.205 mmol) obtained in Example 1 was dissolved in tetrahydrofuran (1.5 mL). To the solution, a solution of lithium hydroxide monohydrate (manufactured by Sigma-Aldrich Corp., 0.086 g, 2.05 mmol) in water (0.5 mL) was added, and the mixture was stirred for 1 hour. Because the progression of the reaction was unable to be confirmed, ethanol (1 mL) was added thereto, and the mixture was stirred at 60° C. for 2 hours. Water was added to the reaction mixture, and the aqueous layer was washed twice with ethyl acetate. The pH of the aqueous layer was adjusted to approximately 4 with 1 mol/L hydrochloric acid, followed by extraction with ethyl acetate twice and a mixed solvent of chloroform/methanol=9/1 once. The obtained organic layer was dried over anhydrous magnesium sulfate and filtered. The filtrate was concentrated under reduced pressure to obtain a crude product of 10,10'-(1-methylazetidine-3,3-diyl)bis(decanoic acid).

ESI-MS m/z: 410 (M−H)$^-$

Step 2

10,10'-(1-Methylazetidine-3,3-diyl)bis(decanoic acid) obtained in step 1 was dissolved in dichloromethane (1.5 mL). To the solution, (Z)-non-2-en-1-ol (manufactured by Tokyo Chemical Industry Co., Ltd., 0.138 g, 0.972 mmol), 1-ethyl-3-(3-dimethylaminopropyl)carbodiimide hydrochloride (0.140 g, 0.729 mmol), and dimethylaminopyridine (0.0590 g, 0.486 mmol) were added in this order, and the mixture was reacted overnight at room temperature. Water was added to the reaction mixture, followed by extraction with ethyl acetate. The organic layer was washed with saturated saline, dried over anhydrous magnesium sulfate and filtered. The filtrate was concentrated under reduced pressure, and the obtained residue was purified by silica gel column chromatography (NH silica gel, hexane/ethyl acetate=99/2 to 80/20) to obtain compound 2 (0.0640 g, yield: 47%).

ESI-MS m/z: 660 (M+H)$^+$; 1H-NMR (CDCl3) δ: 0.88 (t, J=7.0 Hz, 6H), 1.12-1.20 (m, 4H), 1.22-1.41 (m, 32H), 1.50-1.56 (m, 4H), 1.56-1.71 (m, 8H), 2.10 (dd, J=14.4, 7.2

Hz, 4H), 2.30 (t, J=7.6 Hz, 4H), 2.36 (s, 3H), 3.01 (s, 4H), 4.62 (d, J=6.8 Hz, 4H), 5.49-5.55 (m, 2H), 5.61-5.67 (m, 2H).

Reference Example 2

Dinonyl 13,13-bis(hydroxymethyl)pentacosanedioate (Compound IIf-2)

Compound IIf-2 (0.180 g, yield: 7%) was obtained in the same way as in Reference Example 1 by using 12-bromododecanoic acid (manufactured by Sigma-Aldrich Corp., 5.00 g, 17.9 mmol) instead of 10-bromodecanoic acid.
ESI-MS m/z: 726 (M+H)$^+$;

Example 3

Dinonyl 12,12'-(1-methylazetidine-3,3-diyl)didodecanoate (Compound 3)

Compound 3 (0.120 g, yield: 67%) was obtained in the same way as in Example 1 by using compound IIf-2 (0.180 g, 0.248 mmol) obtained in Reference Example 2 instead of compound IIf-1 obtained in Reference Example 1.
ESI-MS m/z: 720 (M+H)$^+$; $^1$H-NMR (CDCl$_3$) δ: 0.88 (t, J=6.8 Hz, 6H), 1.11-1.20 (m, 4H), 1.23-1.35 (m, 52H), 1.49-1.55 (m, 4H), 1.57-1.66 (m, 8H), 2.29 (t, J=7.6 Hz, 4H), 2.31 (s, 3H), 2.94 (s, 4H), 4.06 (t, J=6.7 Hz, 4H).

Example 4

Di((Z)-non-2-en-1-yl) 12,12'-(1-methylazetidine-3,3-diyl)didodecanoate (compound 4)

Compound 4 (0.0390 g, yield: 36%) was obtained in the same way as in Example 2 by using compound 3 obtained in Example 3 instead of compound 1 obtained in Example 1.
ESI-MS m/z: 716 (M+H)$^+$; $^1$H-NMR (CDCl$_3$) δ: 0.88 (t, J=6.8 Hz, 6H), 1.10-1.21 (m, 4H), 1.21-1.39 (m, 44H), 1.51-1.67 (m, 8H), 2.10 (q, J=6.9 Hz, 4H), 2.30 (t, J=7.6 Hz, 4H), 2.42 (s, 3H), 3.11 (s, 4H), 4.62 (dt, J=6.8, 0.6 Hz, 4H), 5.49-5.56 (m, 2H), 5.61-5.67 (m, 2H).

Example 5

A composition was prepared as follows using compound 1 obtained in Example 1. The nucleic acid used was anti-HPRT1 siRNA silencing hypoxanthine-guanine phosphoribosyltransferase 1 (hereinafter referred to as HPRT1) gene and consisted of a sense strand [5'-rGrCrCrArGrArCrUrU-rUrGrUrUrGrArUrUrGrA-3'(sugars attached to the bases with r are ribose): SEQ ID NO: 1] and an antisense strand [5'-rArAmArUmCrCmArAmCrAmArAmGrUm-CrUmGrGmCmUmU-3' (sugars attached to the bases with r and m are ribose and ribose with the hydroxy group at position 2' substituted with a methoxy group, respectively): SEQ ID NO: 2]. This nucleic acid was obtained from GeneDesign, Inc. (hereinafter referred to as HPRT1 siRNA). The nucleic acid was used after being adjusted to 24 mg/mL with distilled water.
Each sample was weighed to be compound 1/PEG-DMPE Na (manufactured by NOF Corp.)=57.3/5.52 (numerical units for all: mmol/L), and suspended in an aqueous solution containing hydrochloric acid and ethanol. A homogenous suspension was obtained by repeating stirring with a vortex stirring mixer and heating. The obtained suspension was passed through a 0.05-µm polycarbonate membrane filter at room temperature to obtain a dispersion of compound 1/PEG-DMPE Na particles (liposomes). The average particle size of the obtained liposomes was measured with a particle size measurement apparatus to confirm that the average particle size fell within the range of 30 nm to 100 nm. The obtained liposome dispersion and the HPRT1 siRNA solution were mixed at a ratio of liposome dispersion:HPRT1 siRNA solution=3:1. A 29-fold amount of distilled water was further added thereto and mixed to prepare a compound 1/PEG-DMPE Na/HPRT1 siRNA complex dispersion.

Each sample was weighed to be compound 1/PEG-DMPE Na (manufactured by NOF Corp.)/DSPC (manufactured by NOF Corp.)/cholesterol (manufactured by NOF Corp.)=8.947/0.147/5.981/14.355 (numerical units for all: mmol/L), and dissolved in ethanol to prepare a lipid membrane constituent solution.

A 4-fold amount of ethanol was further added to the obtained lipid membrane constituent solution, and the mixture and the obtained compound 1/PEG-DMPE Na/HPRT1 siRNA complex dispersion were mixed at a ratio of 2:3 and further mixed with a several-fold amount of distilled water to obtain a crude preparation.

The obtained crude preparation was concentrated using Amicon Ultra (manufactured by Merck Millipore), then diluted with physiological saline and filtered using a 0.2-µm filter (manufactured by Toyo Roshi Kaisha, Ltd.) in a clean bench. The siRNA concentration of the obtained preparation was measured, and the preparation was diluted with physiological saline according to an administration concentration to obtain preparation 1 (composition containing compound 1 and HPRT1 siRNA).

Example 6

Preparations 2 and 3 (compositions containing compounds 2 and 3, respectively, and HPRT1 siRNA) were obtained in the same way as in Example 5 using compounds 2 and 3, respectively, which were obtained in Examples 2 and 3.

The average particle sizes of the preparations 1 to 3 (compositions) obtained in Examples 5 and 6 were measured using a particle size measurement apparatus. The results are shown in Table 4.

TABLE 4

| | Compound No. | | |
|---|---|---|---|
| | 1 | 2 | 3 |
| | Preparation No. | | |
| | 1 | 2 | 3 |
| Particle size of obtained preparation (nm) | 101 | 109 | 114 |

Example 7

A compound 1/PEG-DMPE Na/HPRT1 siRNA complex dispersion was prepared in the same way as in Example 5.

Each sample was weighed to be compound 1/PEG-DMPE Na (manufactured by NOF Corp.)/cholesterol (manufactured by NOF Corp.)=8.947/0.147/20.336 (numerical units for all: mmol/L), and dissolved in ethanol to prepare a lipid membrane constituent solution.

A 4-fold amount of ethanol was further added to the obtained lipid membrane constituent solution, and the mixture and the obtained compound 1/PEG-DMPE Na/HPRT1 siRNA complex dispersion were mixed at a ratio of 2:3 and further mixed with a several-fold amount of distilled water to obtain a crude preparation.

The obtained crude preparation was concentrated using Amicon Ultra (manufactured by Merck Millipore), then diluted with physiological saline and filtered using a 0.2-μm filter (manufactured by Toyo Roshi Kaisha, Ltd.) in a clean bench. The siRNA concentration of the obtained preparation was measured, and the preparation was diluted with physiological saline according to an administration concentration to obtain preparation 4 (composition containing compound 1 and HPRT1 siRNA).

Example 8

Preparations 5 to 8 (compositions containing compounds 2 to 4, respectively, and HPRT1 siRNA) were obtained in the same way as in Example 7 using compounds 2 to 4, respectively, which were obtained in Examples 2 to 4.

The average particle sizes of the preparations (compositions) obtained in Examples 7 and 8 were measured using a particle size measurement apparatus. The results are shown in Table 5.

TABLE 5

| | Compound No. | | | |
|---|---|---|---|---|
| | 1 | 2 | 3 | 4 |
| | Preparation No. | | | |
| | 4 | 5 | 6 | 7 |
| Particle size of obtained preparation (nm) | 115 | 118 | 118 | 100 |

Test Example 1

Preparations 1 to 3 (compositions containing compounds 1 to 3, respectively, and HPRT1 siRNA) obtained in Examples 5 and 6 were evaluated by a method described below in order to examine their activity.

A human pancreatic cancer cell line MIA-PaCa2 and a human lung cancer cell line NCI-H358 were inoculated at 7500 cells/80 uL/well into a DMEM medium (Nacalai Tesque, Inc., 08458-45) containing 10% fetal bovine serum (FBS) and a RPMI1640 medium (Nacalai Tesque, Inc., 30264-85) containing 10% fetal bovine serum (FBS), respectively, and cultured under conditions of 37° C. and 5% CO2 for 24 hours. Then, each of the preparations prepared in Examples 5 and 6 was diluted with an Opti-MEM medium (Thermo Fisher Scientific Inc., 11058021) to be a final concentration of 0.3 to 100 nM in terms of a siRNA concentration, and 20 uL of each dilution was added to the cells. For a negative control, 20 uL of an Opti-MEM medium was added to the cells.

The cells treated with each preparation were cultured in a 5% C02 incubator of 37° C. for 24 hours and washed with ice-cold phosphate buffered saline (PBS). Total RNA was recovered by using Thermo Fisher Cells-to-Ct Kit (Thermo Fisher Scientific Inc., AM1729) according to the attached instruction manual, and cDNA was prepared.

The obtained cDNA was used as a template for PCR reaction, and PCR amplification was performed in a manner specific for each of HPRT1 gene and GAPDH (D-glyceraldehyde-3-phosphate dehydrogenase) gene, which is a gene constitutively expressed, by TaqMan PCR (TaqMan Gene Expression, 4331182) using Applied Biosystems QuantStudio 12K Flex (Applied Biosystems, Inc.), to quantify mRNA levels. The PCR reaction conditions conformed to the attached instruction manual of TaqMan Gene Expression. The mRNA level of a specimen was calculated as a relative ratio of a calculated HPRT1 mRNA level with respect to a GAPDH mRNA level with the value in a negative control treatment group defined as 1. The results about the HPRT1 mRNA level are shown in FIGS. 1 and 2.

Test Example 2

Preparations 4 to 8 (compositions containing compounds 1 to 4, respectively, and HPRT1 siRNA) obtained in Examples 7 and 8 were evaluated in the same way as in Test Example 1 in order to examine their activity. The results about the HPRT1 mRNA level are shown in FIGS. 3 and 4.

As is evident from FIGS. 1, 2, 3 and 4, the HPRT1 mRNA level was decreased by the administration of the preparations 1 to 7 obtained in Examples 5 to 8.

These results demonstrated that the composition of the present invention can introduce a nucleic acid into a cell or the like, and the cationic lipid of the present invention facilitates delivering a nucleic acid into a cell in vivo.

INDUSTRIAL APPLICABILITY

A composition containing the cationic lipid of the present invention and a nucleic acid can easily introduce the nucleic acid, for example, into a cell, by its administration to a mammal or the like.

Free Text of Sequence Listing

SEQ ID NO: 1: Hypoxanthine-guanine phosphoribosyltransferase 1 siRNA sense strand SEQ ID NO: 2: Hypoxanthine-guanine phosphoribosyltransferase 1 siRNA antisense strand

The invention claimed is:

1. A compound represented by formula (I):

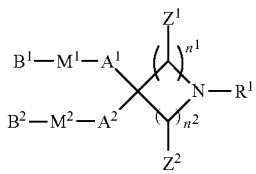

(I)

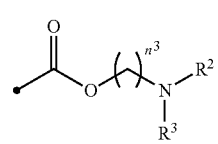

(A)

wherein $R^1$ is a hydrogen atom, C1-C3 alkyl, hydroxyC2-C4 alkyl, di-C1-C3 alkylaminoC2-C4 alkyl, formula (A):

wherein $R^2$ and $R^3$ are, the same or different, a hydrogen atom or C1-C3 alkyl, or $R^2$ and $R^3$, together with the nitrogen atom to which they are attached, may form a C2-C6 nitrogen-containing heterocycle, and $n^3$ is an integer from 2 to 6, or formula (B):

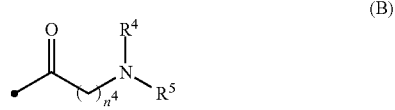

wherein $R^4$ and $R^5$ are, the same or different, a hydrogen atom or C1-C3 alkyl, or $R^4$ and $R^5$, together with the nitrogen atom to which they are attached, may form a C2-C6 nitrogen-containing heterocycle, and $n^4$ is an integer from 1 to 6;

$n^1$ is an integer from 0 to 4; $n^2$ is an integer from 1 to 4, provided that the case where $n^1$ is 0 and $n^2$ is 1 is excluded;

$Z^1$ is, independently for each carbon atom bonded thereto, a hydrogen atom or C1-C3 alkyl;

$Z^2$ is, independently for each carbon atom bonded thereto, a hydrogen atom or C1-C3 alkyl;

$A^1$ and $A^2$ are, the same or different, linear or branched C8-C20 alkylene or C8-C20 alkenylene, or C6-C18 alkyleneoxyC1-C3 alkylene or C6-C18 alkenyleneoxyC1-C3 alkylene;

$M^1$ and $M^2$ are, the same or different, selected from the group consisting of —OC(O)—, —C(O)O—, —SC(O)—, —C(O)S—, —OC(S)—, —C(S)O—, —SS—, —C($R^6$)=N—, —N=C($R^6$)—, —C($R^6$)=N—O—, —O—N=C($R^6$)—, —N($R^6$)C(O)—, —C(O)N($R^6$)—, —N($R^6$)C(S)—, —C(S)N($R^6$)—, —N($R^6$)C(O)N($R^7$)—, —N($R^6$)C(O)O—, —OC(O)N($R^6$)—, and —OC(O)O—;

$R^6$ and $R^7$ are, the same or different, a hydrogen atom or C1-C4 alkyl; and $B^1$ and $B^2$ are, the same or different, linear or branched C1-C16 alkyl or C2-C16 alkenyl or a pharmaceutically acceptable salt thereof.

2. The compound according to claim 1 or a pharmaceutically acceptable salt thereof, wherein $M^1$ and $M^2$ are, the same or different, selected from the group consisting of —OC(O)—, —C(O)O—, —N($R^6$)C(O)—, and —C(O)N($R^6$)—.

3. The compound according to claim 2 or a pharmaceutically acceptable salt thereof, wherein $M^1$ and $M^2$ are, the same or different, —OC(O)— or —C(O)O—.

4. The compound according to claim 1 or a pharmaceutically acceptable salt thereof, wherein $A^1$ and $A^2$ are, the same or different, linear or branched C8-C20 alkylene or C8-C20 alkenylene.

5. The compound according to claim 1 or a pharmaceutically acceptable salt thereof, wherein $B^1$-$M^1$-$A^1$- and $B^2$-$M^2$-$A^2$- are the same.

6. The compound according to claim 1 or a pharmaceutically acceptable salt thereof, wherein $R^1$ is C1-C3 alkyl.

7. The compound according to claim 1 or a pharmaceutically acceptable salt thereof, wherein $n^1$ is 1, and $n^2$ is an integer from 1 to 3.

8. The compound according to claim 1 or a pharmaceutically acceptable salt thereof, wherein both of $n^1$ and $n^2$ are 1.

9. A composition comprising the compound according to claim 1 or a pharmaceutically acceptable salt thereof and a nucleic acid.

10. The composition according to claim 9, further comprising a neutral lipid and/or a polymer.

11. The composition according to claim 9, wherein the nucleic acid is a nucleic acid having a silencing effect on a target gene through the use of RNA interference (RNAi).

12. The composition according to claim 11, wherein the target gene is a gene expressed in the liver, the lung, the kidney, the digestive tract, the central nervous system, or the spleen.

13. The composition according to claim 9, wherein the composition is for intravenous administration.

14. A medicament comprising the composition according to claim 9.

15. A method for therapeutically treating a disease related to the liver, the lung, the kidney, the digestive tract, the central nervous system, or the spleen, comprising administering the composition according to claim 9 to a patient in need thereof.

* * * * *

SEQUENCE LISTING

<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: HPRT1 siRNA sense

<400> SEQUENCE: 1

```
gccagacuuu guuggauuug a                                          21

<210> SEQ ID NO 2
<211> LENGTH: 21
<212> TYPE: RNA
<213> ORGANISM: Artificial Sequence
<220> FEATURE:
<223> OTHER INFORMATION: HPRT1 siRNA antisense
<220> FEATURE:
<221> NAME/KEY: modified_base
<222> LOCATION: (3)..(3)
<223> OTHER INFORMATION: am
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (7)..(7)
<223> OTHER INFORMATION: am
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: am
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(21)
<223> OTHER INFORMATION: um

<400> SEQUENCE: 2
aaauccaaca aagucuggcu u                                          21
```